United States Patent
Gadwood et al.

(10) Patent No.: US 7,094,900 B2
(45) Date of Patent: Aug. 22, 2006

(54) N-ARYL-2-OXAZOLIDINONES AND THEIR DERIVATIVES

(75) Inventors: Robert C. Gadwood, Portage, MI (US); Jason M. Ochoada, Kalamazoo, MI (US)

(73) Assignee: Pharmacia & Upjohn Company LLC, Kalamazoo, MI (US)

( * ) Notice: Subject to any disclaimer, the term of this patent is extended or adjusted under 35 U.S.C. 154(b) by 234 days.

(21) Appl. No.: 10/632,742

(22) Filed: Aug. 1, 2003

(65) Prior Publication Data

US 2004/0072873 A1  Apr. 15, 2004

Related U.S. Application Data

(60) Provisional application No. 60/402,783, filed on Aug. 12, 2002.

(51) Int. Cl.
*A61K 31/4525* (2006.01)
*A61K 31/454* (2006.01)
*C07D 401/10* (2006.01)

(52) U.S. Cl. ...................... 546/209; 514/326
(58) Field of Classification Search ............... 546/209; 514/326
See application file for complete search history.

(56) References Cited

U.S. PATENT DOCUMENTS

| | | | | |
|---|---|---|---|---|
| 4,705,799 A | 11/1987 | Gregory | | 514/376 |
| 5,043,443 A | 8/1991 | Carlson et al. | | 544/112 |
| 5,164,510 A | 11/1992 | Brickner | | 548/231 |
| 5,182,403 A | 1/1993 | Brickner | | 548/231 |
| 5,225,565 A | 7/1993 | Brickner | | 548/229 |
| 5,231,188 A | 7/1993 | Brickner | | 548/221 |
| 5,247,090 A | 9/1993 | Brickner | | 546/89 |
| 5,523,403 A | 6/1996 | Barbachyn | | 544/137 |
| 5,529,998 A | 6/1996 | Habich et al. | | 514/233.8 |
| 5,547,950 A | 8/1996 | Hutchinson et al. | | 514/252 |
| 5,565,571 A | 10/1996 | Barbachyn et al. | | 546/144 |
| 5,627,181 A | 5/1997 | Riedl et al. | | 514/236.8 |
| 5,652,238 A | 7/1997 | Brickner et al. | | 514/235.8 |
| 5,684,023 A | 11/1997 | Riedl et al. | | 514/337 |
| 5,688,792 A | 11/1997 | Barbachyn et al. | | 514/235.5 |
| 5,698,574 A | 12/1997 | Riedl et al. | | 514/376 |
| 5,792,765 A | 8/1998 | Riedl et al. | | 514/236.8 |
| 5,827,857 A | 10/1998 | Riedl et al. | | 514/301 |
| 5,843,967 A | 12/1998 | Riedl et al. | | 514/340 |
| 5,861,413 A | 1/1999 | Habich et al. | | 514/312 |
| 5,869,659 A | 2/1999 | Stolle et al. | | 544/114 |
| 5,952,324 A | 9/1999 | Barbachyn et al. | | 514/211 |
| 5,968,962 A | 10/1999 | Thomas et al. | | 514/376 |
| 5,981,528 A | 11/1999 | Gravestock | | 514/252 |
| 6,043,266 A | 3/2000 | Ennis et al. | | 514/376 |
| 6,051,716 A | 4/2000 | Hutchinson et al. | | 548/229 |
| 6,069,145 A | 5/2000 | Betts | | 514/252 |
| 6,069,160 A | 5/2000 | Stolle et al. | | 514/367 |
| 6,110,936 A | 8/2000 | Gravestock | | 514/315 |
| 6,166,056 A | 12/2000 | Thomas et al. | | 514/376 |
| 6,194,441 B1 | 2/2001 | Roberts et al. | | 514/340 |
| 6,239,152 B1 | 5/2001 | Gordeev et al. | | 514/340 |
| 6,271,383 B1 | 8/2001 | Gravestock | | 546/209 |
| 6,313,307 B1 | 11/2001 | Ennis et al. | | 548/229 |

FOREIGN PATENT DOCUMENTS

| | | |
|---|---|---|
| WO | WO 94/01110 | 1/1994 |
| WO | WO 95/07271 | 3/1995 |
| WO | WO 95/25106 | 9/1995 |
| WO | WO 96/13502 | 5/1996 |
| WO | WO 96/15130 | 5/1996 |
| WO | WO 96/23788 | 8/1996 |
| WO | WO 96/35691 | 11/1996 |
| WO | WO 97/09328 | 3/1997 |
| WO | WO 97/10223 | 3/1997 |
| WO | WO 97/19089 | 5/1997 |
| WO | WO 97/30981 | 8/1997 |
| WO | WO 97/30995 | 8/1997 |
| WO | WO 98/54161 | 12/1998 |
| WO | WO 99/03846 | 1/1999 |
| WO | WO 99/24428 | 5/1999 |
| WO | WO 99/29688 | 6/1999 |
| WO | WO 99/37641 | 7/1999 |
| WO | WO 99/37652 | 7/1999 |
| WO | WO 99/40094 | 8/1999 |
| WO | WO 00/21960 | 4/2000 |
| WO | WO 01/40236 A2 | 6/2001 |
| WO | WO 01/81350 A1 | 11/2001 |
| WO | WO 01/94342 A1 | 12/2001 |

OTHER PUBLICATIONS

Brickner, S.J., et al., "*Synthesis and Antibacterial Activity of U-100592 and U-100766, Two Oxazolidinone Antibacterial Agents for the Potential Treatment of Multidrug-Resistant Gram-Positive Bacterial Infections*", Jr. Med. Chem., vol. 39, pp. 673-679 (1996).
Leznoff, C.C., P.I. Svirskaya and V. Yedidia, "*Fluorinated Heterocyclic Compounds. 4-Fluoro-2-pyridone*", J. Heterocyclic Chem., vol. 22, p. 145-147 (Jan.-Feb. 1985).
Sprecher, M., et al., "*Monosubstituted 2,2'-Bipyridines*", Org. Prep and Proceed Int., vol. 26(6), p. 696-701 (1994).

*Primary Examiner*—Patricia L. Morris
(74) *Attorney, Agent, or Firm*—Robert N. Young; Charles W. Ashbrook

(57) ABSTRACT

The present invention provides antibacterial agents of formula I described herein.

18 Claims, No Drawings

N-ARYL-2-OXAZOLIDINONES AND THEIR DERIVATIVES

CROSS-REFERENCE TO RELATED APPLICATIONS

This application claims the benefit of the following provisional application: U.S. Ser. No. 60/402,783, filed Aug. 12, 2002, under 35USC119(e)(i), which is incorporated herein by reference in its entirety.

The present invention relates to novel N-Aryl-2-oxazolidinones, derivatives thereof, and their preparations. These compounds have potent antibacterial activity.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant *staphylococci* and *streptococci*, anaerobic organisms such as bacteroides and *clostridia* species, and acid-fast organisms such as *Mycobacterium tuberculosis* and *Mycobacterium avium*.

SUMMARY OF THE INVENTION

In one aspect the invention features compounds of formula I

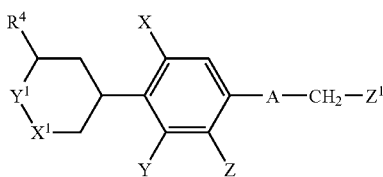

I or a pharmaceutically acceptable salt thereof wherein:
A is structure i, ii, iii, or iv

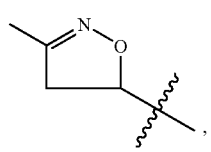

i

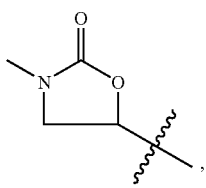

ii

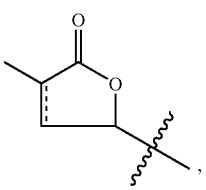

iii

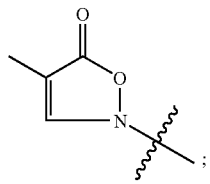

iv $X^1$ and $Y^1$ together form the group —C(=O)N($R^5$)— wherein $X^1$ is either C(=O) (and $Y^1$ is $NR^5$) or $X^1$ is $NR^5$ (and $Y^1$ is C(=O)).

$Z^1$ is
  (a) NHC(=O)$R^1$,
  (b) NHC(=S)$R^1$,
  (c) NH-$het^1$,
  (d) O-$het^1$,
  (e) S-$het^1$, or
  (f) $het^2$;

$R^1$ is
  (a) $NH_2$,
  (b) $NHC_{1-4}$alkyl,
  (c) $C_{1-4}$alkyl,
  (d) $C_{2-4}$alkenyl,
  (e) —$CH_2$C(=O)$C_{1-4}$alkyl,
  (f) $OC_{1-4}$alkyl,
  (g) $SC_{1-4}$alkyl, or
  (h) $C_{3-6}$cycloalkyl;

Each X, Y, and Z is independently selected from
  (a) H,
  (b) Cl,
  (c) F, or
  (d) $CH_3$ $R^4$ is
  (a) H,
  (b) $C_{1-4}$alkyl,
  (c) $OC_{1-4}$alkyl,
  (d) $SC_{1-4}$alkyl, or
  (e) $NHC_{1-4}$alkyl;

$R^5$ is
  (a) H,
  (b) $C_{1-4}$alkyl, or
  (c) —$(CH_2)_n$—$W_1$—$(CH_2)_n$-$Z^3$;

$W_1$ is
  (a) —$CH_2$—,
  (b) —CH=CH—,
  (c) —C≡C—, or (d)

$Z^3$ is (a)

W$_2$ is
  (a) —O—,
  (b) —N(R$_{25}$)—, or
  (c) —C(=O)—N(R$_{25}$)—, wherein either the carbon or the nitrogen atom of the amide may be bound to a carbon atom of the phenyl ring of Z$^3$;

R$_{22}$ is (CH$_2$)$_t$NR$_{23}$R$_{24}$, H, halo, C$_{1-4}$alkyl, —CN, —OH, —O—C$_{1-4}$alkyl, —S(O)$_u$C$_{1-4}$alkyl, and —C(=O)NH$_2$ R$_{23}$ is H or C$_{1-4}$ alkyl;

R$_{24}$ is is H, C$_{1-4}$ alkyl, —S(O)$_2$—C$_{1-4}$alkyl, —C(=O)—C$_{1-4}$ alkyl, —C(=NH)—NH$_2$, —C(=O)—C(HR$_{26}$)—NR$_{27}$R$_{28}$;

R$_{25}$ is H or C$_{1-4}$ alkyl;

R$_{26}$ is H, C$_{1-4}$ alkyl which can be optionally substituted by —OH, —NH$_2$, —NH—C(=NH)—NH$_2$, —SH, —SCH$_3$, —COOH, —C(O)NH$_2$, and phenyl which can be optionally substituted with —OH, imidazole, indole, or R$_{26}$ and R$_{27}$ together with the carbon atom to which R$_{26}$ attaches and the nitrogen atom to which R$_{27}$ attaches form a heterocycloalkyl;

R$_{27}$ is H or C$_{1-4}$ alkyl;

R$_{28}$ is H, C$_{1-4}$ alkyl, —S(O)$_2$—C$_{1-4}$alkyl, —C(=O)—C$_{1-4}$ alkyl, —C(=NH)—NH$_2$, —C(=O)—C(HR$_{26}$)—NR$_{27}$R$_{27}$ t is 0, 1;
u is 0, 1, 2;
n is 1 or 2;

het$^1$ is a C-linked five-(5) or six-(6) membered heterocyclic ring having 1–4 heteroatoms selected from the group consisting of oxygen, sulfur, and nitrogen; het$^1$ being optionally substituted on one or more carbon atoms by 1–2 substituents selected from C$_1$–C$_4$alkyl, amino, C$_1$–C$_4$alkylamino, C$_1$–C$_4$alkyloxy, halogen —CN, =O, =S, and being optionally substituted with C$_1$–C$_4$alkyl;

het$^2$ is a N-linked five-(5) or six-6) membered heterocyclic ring having at least one nitrogen atom, and optionally having one oxygen or sulfur atom; het$^2$ being optionally substituted on one or more carbon atoms by 1–2 substituents selected from C$_1$–C$_4$alkyl, amino, C$_1$–C$_4$alkylamino, C$_1$–C$_4$alkyloxy, halogen —CN, =O, =S, and being optionally substituted with C$_1$–C$_4$alkyl;

heterocycloalkyl is a four (5) or seven (7) membered saturated heterocyclic ring having 1–4 heteroatoms selected from the group consisting of oxygen, sulfur, and nitrogen; heterocycloalkyl being optionally substituted on one or more carbon atoms by 1–2 substituents selected from C$_1$–C$_4$alkyl, amino, C$_1$–C$_4$alkylamino, C$_1$–C$_4$alkyloxy, halogen —CN, =O, =S, and being optionally substituted with C$_1$–C$_4$alkyl;

at each occurrence, alkyl, alkenyl, or cycloalkyl is optionally substituted with 1–3 halo, —OH, —OC$_{1-4}$alkyl, and Aryl refers to phenyl, biphenyl, or naphthyl, optionally substituted with halo, C$_{1-4}$ alkyl, OH, OC$_{1-4}$ alkyl, —CH$_2$NH$_2$, —CH$_2$NH(C$_{1-4}$ alkyl), and S(O)$_u$C$_{1-4}$alkyl.

Embodiments of this aspect of the invention may include one or more of the following. A is formula ii. X is F. Y is F. Z$^1$ is —NH—C(O)R$_1$. R$_1$ is selected from C$_{1-4}$alkyl optionally substituted with 1–3 halo. R$_1$ is C$_{1-4}$alkyl substituted with 1–2 halo. Z$^1$ is —NH—C(S)R$_1$. Y$^1$ is —C(=O)— and X$^1$ is —N(R$_5$)—. X$^1$ is —C(=O)— and Y$^1$ is —N(R$_5$)—. A compound selected from the group consisting of N-({(5S)-3-[3-fluoro-4-(6-oxopiperidin-3-yl)phenyl]-2-oxo-1,3-oxazolidin-5-yl}methyl)acetamide;

N-({(5S)-3-[3-fluoro-4-(6-oxopiperidin-3-yl)phenyl]-2-oxo-1,3-oxazolidin-5-yl}methyl)propanamide;

2,2-dichloro-N-({(5S)-3-[3-fluoro-4-(6-oxopiperidin-3-yl)phenyl]-2-oxo-1,3-oxazolidin-5-yl}methyl)acetamide;

2,2-difluoro-N-({(5S)-3-[3-fluoro-4-(6-oxopiperidin-3-yl)phenyl]-2-oxo-1,3-oxazolidin-5-yl}methyl)ethanethioamide;

2,2-difluoro-N-({(5S)-3-[3-fluoro-4-(6-oxopiperidin-3-yl)phenyl]-2-oxo-1,3-oxazolidin-5-yl}methyl)acetamide;

N-({(5S)-3-[3,5-difluoro-4-(6-oxopiperidin-3-yl)phenyl]-2-oxo-1,3-oxazolidin-5-yl}methyl)acetamide;

2,2-dichloro-N-({(5S)-3-[3,5-difluoro-4-(6-oxopiperidin-3-yl)phenyl]-2-oxo-1,3-oxazolidin-5-yl}methyl)acetamide;

N-({(5S)-3-[3,5-difluoro-4-(6-oxopiperidin-3-yl)phenyl]-2-oxo-1,3-oxazolidin-5-yl}methyl)-2,2-difluoroethanethioamide;

N-({(5S)-3-[3,5-difluoro-4-(6-oxopiperidin-3-yl)phenyl]-2-oxo-1,3-oxazolidin-5-yl}methyl)-2,2-difluoroacetamide;

N-({(5S)-2-oxo-3-[4-(6-oxopiperidin-3-yl)phenyl]-1,3-oxazolidin-5-yl}methyl)acetamide;

N-({(5S)-2-oxo-3-[4-(6-oxopiperidin-3-yl)phenyl]-1,3-oxazolidin-5-yl}methyl)propanamide;

2,2-dichloro-N-({(5S)-2-oxo-3-[4-(6-oxopiperidin-3-yl)phenyl]-1,3-oxazolidin-5-yl}methyl)acetamide;

2,2-difluoro-N-({(5S)-2-oxo-3-[4-(6-oxopiperidin-3-yl)phenyl]-1,3-oxazolidin-5-yl}methyl)ethanethioamide;

2,2-difluoro-N-({(5S)-2-oxo-3-[4-(6-oxopiperidin-3-yl)phenyl]-1,3-oxazolidin-5-yl}methyl)ethanethioamide;

({(5S)-3-[4-(1-methyl-6-oxopiperidin-3-yl)phenyl]-2-oxo-1,3-oxazolidin-5-yl}methyl)acetamide;

N-({(5S)-3-[3-fluoro-4-(2-oxopiperidin-4-yl)phenyl]-2-oxo-1,3-oxazolidin-5-yl}methyl)acetamide;

N-({(5S)-3-[3-fluoro-4-(2-oxopiperidin-4-yl)phenyl]-2-oxo-1,3-oxazolidin-5-yl}methyl)propanamide;

2,2-difluoro-N-({(5S)-3-[3-fluoro-4-(2-oxopiperidin-4-yl)phenyl]-2-oxo-1,3-oxazolidin-5-yl}methyl)ethanethioamide;

N-({(5S)-3-[3,5-difluoro-4-(2-oxopiperidin-4-yl)phenyl]-2-oxo-1,3-oxazolidin-5-yl}methyl)acetamide;

N-({(5S)-3-[3,5-difluoro-4-(2-oxopiperidin-4-yl)phenyl]-2-oxo-1,3-oxazolidin-5-yl}methyl)propanamide;

N-({(5S)-3-[3,5-difluoro-4-(2-oxopiperidin-4-yl)phenyl]-2-oxo-1,3-oxazolidin-5-yl}methyl)-2,2-difluoroethanethioamide;

N-({(5S)-2-oxo-3-[4-(2-oxopiperidin-4-yl)phenyl]-1,3-oxazolidin-5-yl}methyl)acetamide;

2,2-difluoro-N-({(5S)-2-oxo-3-[4-(2-oxopiperidin-4-yl)phenyl]-1,3-oxazolidin-5-yl}methyl)ethanethioamide;

N-({(5S)-2-oxo-3-[4-(2-oxopiperidin-4-yl)phenyl]-1,3-oxazolidin-5-yl}methyl)propanamide;

N-({(5S)-3-[4-(1-methyl-2-oxopiperidin-4-yl)phenyl]-2-oxo-1,3-oxazolidin-5-yl}methyl)acetamide; and 5-{2,6-difluoro-4-[(5R)-2-oxo-5-(1H-1,2,3-triazol-1-ylmethyl)-1,3-oxazolidin-3-yl]phenyl}piperidin-2-one.

In another aspect, the invention features a method for the treatment of microbial infections in mammals including administrating an effective amount of compound of formula 1 to the mammal.

Embodiments of this aspect of the invention feature one or more of the following. The compound is administered to the mammal orally, parenterally, transdermally, or topically in a pharmaceutical composition. The compound is administered in an amount of from about 0.1 to about 100 mg/kg of body weight/day. The compound is administered in an amount of from about 1 to about 50 mg/kg of body weight/day.

In yet another aspect, the invention features a pharmaceutical composition comprising a compound of claim 1 and a pharmaceutically acceptable carrier.

DETAILED DESCRIPTION OF THE INVENTION

The following definitions are used, unless otherwise described.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "halo" refers to a halogen atom selected from Cl, Br, I, and F.

The term "alkyl" refers to both straight- and branched-chain moieties. Unless otherwise specifically stated alkyl moieties include between 1 and 6 carbon atoms.

The term "alkenyl" refers to both straight- and branched-chain moieties containing at least one —C═C—. Unless otherwise specifically stated alkenyl moieties include between 1 and 6 carbon atoms.

The term "alkynyl" refers to both straight- and branched-chain moieties containing at least one —C≡C—. Unless otherwise specifically stated alkynyl moieties include between 1 and 6 carbon atoms.

The term "alkoxy" refers to —O-alkyl groups.

The term "cycloalkyl" refers to a cyclic alkyl moiety. Unless otherwise specifically stated cycloalkyl moieties will include between 3 and 7 carbon atoms.

The term "cycloalkenyl" refers to a cyclic alkenyl moiety. Unless otherwise specifically stated cycloalkenyl moieties will include between 3 and 7 carbon atoms and at least one —C═C— group within the cyclic ring.

The term "amino" refers to —NH$_2$.

The term "aryl" refers to phenyl and naphthyl.

The term "het" refers to mono- or bicyclic ring systems containing at least one heteroatom selected from O, S, and N. Each monocyclic ring may be aromatic, saturated, or partially unsaturated. A bicyclic ring system may include a monocyclic ring containing at least one heteroatom fused with a cycloalkyl or aryl group. A bicyclic ring system may also include a monocyclic ring containing at least one heteroatom fused with another het, monocyclic ring system. The term het encompasses the terms het[1], het[2], and heterocycloalkyl, described herein.

Examples of "het" include, but are not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazolyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo[2.2.1]heptyl.

The term "heteroaryl" refers to an aromatic het, examples of which include, but are not limited to, pyridine and thiophene.

The term "substituted alkyl" refers to an alkyl moiety including 1–4 substituents selected from halo, het, cycloalyl, cycloalkenyl, aryl, —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, and —SNQ$_{10}$Q$_{10}$. Each of the het, cycloalkyl, cycloalkenyl, and aryl may be optionally substituted with 1–4 substituents independently selected from halo and Q$_{15}$.

The term "substituted aryl" refers to an aryl moiety having 1–3 substituents selected from —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted het" refers to a het moiety including 1–4 substituents selected from —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The substituted het also may be substituted by one or more ═O or ═S substituents provided that the O or S are bound to ring atoms capable of supporting a double bond between the ring atom and O or S. The het, cycloalkyl, cycloalkenyl, and aryl may be optionally substituted with 1–3 substituents selected from halo and Q$_{15}$.

The term "substituted alkenyl" refers to a alkenyl moiety including 1–3 substituents —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted alkoxy" refers to an alkoxy moiety including 1–3 substituents —OQ$_{10}$, —SQ$_{10}$, —S(O)$_2$Q$_{10}$, —S(O)Q$_{10}$, —OS(O)$_2$Q$_{10}$, —C(═NQ$_{10}$)Q$_{10}$, —SC(O)Q$_{10}$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(O)C(Q$_{16}$)$_2$OC(O)Q$_{10}$, —CN, ═O, ═S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, —NO$_2$, —SNQ$_{10}$Q$_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and Q$_{15}$.

The term "substituted cycloalkenyl" refers to a cycloalkenyl moiety including 1–3 substituents —OQ$_{10}$, —SQ$_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

The term "substituted amino" refers to an amino moiety in which one or both of the amino hydrogens are replaced with a group selected from —$OQ_{10}$, —$SQ_{10}$, —$S(O)_2Q_{10}$, —$S(O)Q_{10}$, —$OS(O)_2Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

Each $Q_{10}$ is independently selected from —H, alkyl, cycloalkyl, het, cycloalkenyl, and aryl. The het, cycloalkyl, cycloalkenyl, and aryl may be optionally substituted with 1–3 substituents selected from halo and $Q_{13}$.

Each $Q_{11}$ is independently selected from —H, halo, alkyl, aryl, cycloalkyl, and het. The alkyl, cycloalkyl, and het may be optionally substituted with 1–3 substituents independently selected from halo, —$NO_2$, —CN, =S, =O, and $Q_{14}$. The aryl may be optionally substituted with 1–3 substituents independently selected from halo, —$NO_2$, —CN, and $Q_{14}$.

Each $Q_{13}$ is independently selected from $Q_{11}$, —$OQ_{11}$, —$SQ_{11}$, —$S(O)_2Q_{11}$, —$S(O)Q_{11}$, —$OS(O)_2Q_{11}$, —$C(=NQ_{11})Q_{11}$, —$SC(O)Q_{11}$, —$NQ_{11}Q_{11}$, —$C(O)Q_{11}$, —$C(S)Q_{11}$, —$C(O)OQ_{11}$, —$OC(O)Q_{11}$, —$C(O)NQ_{11}Q_{11}$, —$C(O)C(Q_{16})_2OC(O)Q_{10}$, —CN, =O, =S, —$NQ_{11}C(O)Q_{11}$, —$NQ_{11}C(O)NQ_{11}Q_{11}$, —$S(O)_2NQ_{11}Q_{11}$, —$NQ_{11}S(O)_2Q_{11}$, —$NQ_{11}S(O)Q_{11}$, —$NQ_{11}SQ_{11}$, —$NO_2$, and —$SNQ_{11}Q_{11}$, provided that $Q_{13}$ is not =O or =S when $Q_{10}$ is aryl or a het lacking any atom capable of forming a double bond with O or S.

Each $Q_{14}$ is —H or a substituent selected from alkyl, cycloalkyl, cycloalkenyl, phenyl, or naphthyl, each optionally substituted with 1–4 substituents independently selected from —F, —Cl, —Br, —I, —$OQ_{16}$, —$SQ_{16}$, —$S(O)_2Q_{16}$, —$S(O)Q_{16}$, —$OS(O)_2Q_{16}$, —$NQ_{16}Q_{16}$, —$C(O)Q_{16}$, —$C(S)Q_{16}$, —$C(O)OQ_{16}$, —$NO_2$, —$C(O)NQ_{16}Q_{16}$, —CN, —$NQ_{16}C(O)Q_{16}$, —$NQ_{16}C(O)NQ_{16}Q_{16}$, —$S(O)_2NQ_{16}Q_{16}$, and —$NQ_{16}S(O)_2Q_{16}$. The alkyl, cycloalkyl, and cycloalkenyl may be further substituted with =O or =S.

Each $Q_{15}$ is alkyl, cycloalkyl, cycloalkenyl, het, phenyl, or naphthyl, each optionally substituted with 1–4 substituents independently selected from —F, —Cl, —Br, —I, —$OQ_{16}$, —$SQ_{16}$, —$S(O)_2Q_{16}$, —$S(O)Q_{16}$, —$OS(O)_2Q_{16}$, —$C(=NQ_{16})Q_{16}$, —$SC(O)Q_{16}$, —$NQ_{16}Q_{16}$, —$C(O)Q_{16}$, —$C(S)Q_{16}$, —$C(O)OQ_{16}$, —$OC(O)Q_{16}$, —$C(O)NQ_{16}Q_{16}$, —$C(O)C(Q_{16})_2OC(O)Q_{16}$, —CN, —$NQ_{16}C(O)Q_{16}$, —$NQ_{16}C(O)NQ_{16}Q_{16}$, —$S(O)_2NQ_{16}Q_{16}$, —$NQ_{16}S(O)_2Q_{16}$, —$NQ_{16}S(O)Q_{16}$, —$NQ_{16}SQ_{16}$, —$NO_2$, and —$SNQ_{16}Q_{16}$. The alkyl, cycloalkyl, and cycloalkenyl may be further substituted with =O or =S.

Each $Q_{16}$ is independently selected from —H, alkyl, and cycloalkyl. The alkyl and cycloalkyl may optionally include 1–3 halos.

Mammal refers to human or animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature).

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

The compounds of Formula I of this invention contain a chiral center, such as at C-5 of the isoxazoline ring, and as such there exist two enantiomers or a racemic mixture of both. This invention relates to both the enantiomers, as well as mixtures containing both the isomers. In addition, depending on substituents, additional chiral centers and other isomeric forms may be present in compounds of formula I, and this invention embraces all possible stereoisomers and geometric forms.

The compounds of this invention are useful for treatment of microbial infections in humans and other warm blooded animals, under both parenteral and oral administration.

The pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 four times per day.

The compounds according to this invention may be administered parenterally, i.e., by injection, for example, by intravenous injection or by other parenteral routes of administration. Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds according to this invention are advantageously administered orally in solid and liquid dosage forms.

As a topical treatment an effective amount of Formula I is admixed in a pharmaceutically acceptable gel or cream vehicle that can be applied to the patient's skin at the area of treatment. Preparation of such creams and gels is well known in the art and can include penetration enhancers.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA.

Compounds of formula I may be produced by methods known to those skilled in the art. For instance the compounds of formula I may be synthesized via schemes 1–4 shown below.

Scheme 1

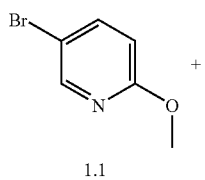

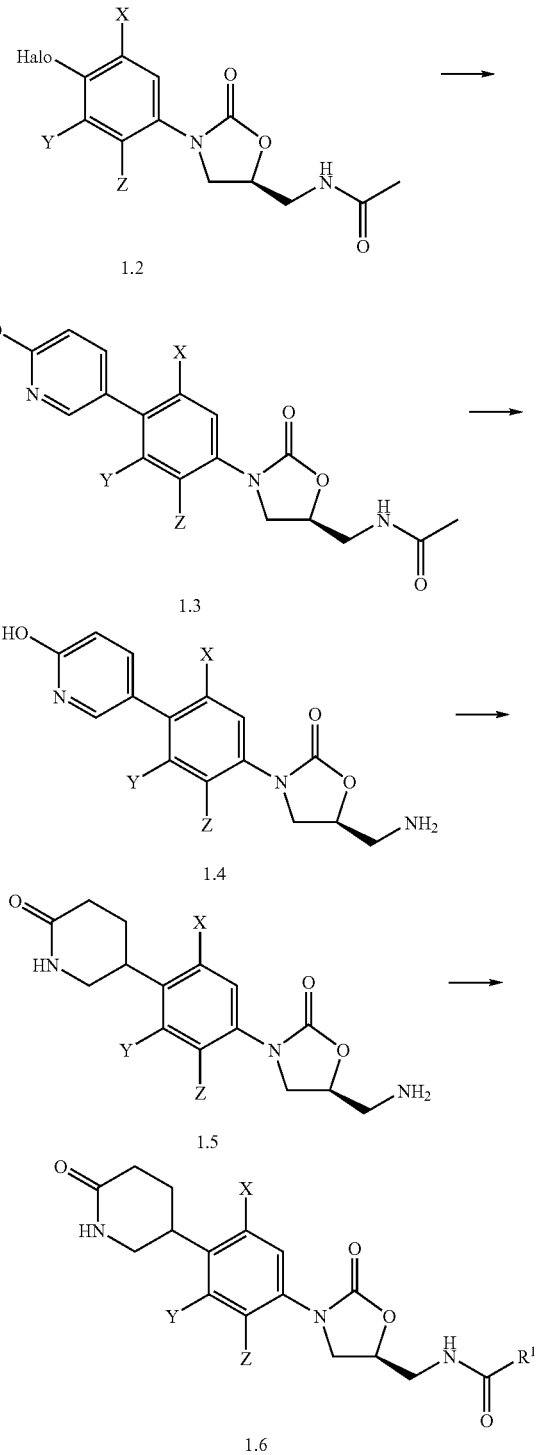

Referring to scheme 1, a functionalized pyridine 1.1 including an alkoxy moiety is coupled via a Suzuki type coupling to an N-phenyl-2-oxazolidinone-5-carboxamide 1.2 to form an alkoxy substituted pyridyl-4-phenyl-2-oxazolidinone-5-methyl amide 1.3. Acidic cleavage of the alkoxy substituent with HCl/dioxane provides the hydroxypyridine 1.4. Hydrogenation of the alcohol substituted pyridyl-4-phenyl-2-oxazolidinone-5-methyl amine 1.4 affords the N-phenyl-2-oxazolidinone-5-methylamine lactam 1.5 and acylation of the oxazolidinone C-5 methyl amine provides the desired lactam 1.6. Although scheme 1 illustrates a synthesis for preparing N-({(5S)-3-[4-(6-oxopiperidin-3-yl)phenyl]-2-oxo-1,3-oxazolidin-5-yl}methyl) derivatives, N-({(5S)-3-[4-(2-oxopiperidin-4-yl)phenyl]-2-oxo-1,3-oxazolidin-5-yl}methyl) derivatives may be synthesized by utilizing the appropriate pyridine starting material.

N-phenyl-2-oxazolidinone-5-carboxamide starting materials may be produced by known methods. For instance, compounds including X=Y=Z=H are described by U.S. Pat. No. 4,705,799, which is hereby incorporated by reference. Compounds including the phenyl substituents (X=F, Y=Z=H) and (X=Y=F, Z=H) are described in U.S. Pat. No. 5,523,403, which is hereby incorporated by reference. Scheme 2, shown below, describes a procedure for producing staring materials in which the pheny substituents are X=Y=Z=F.

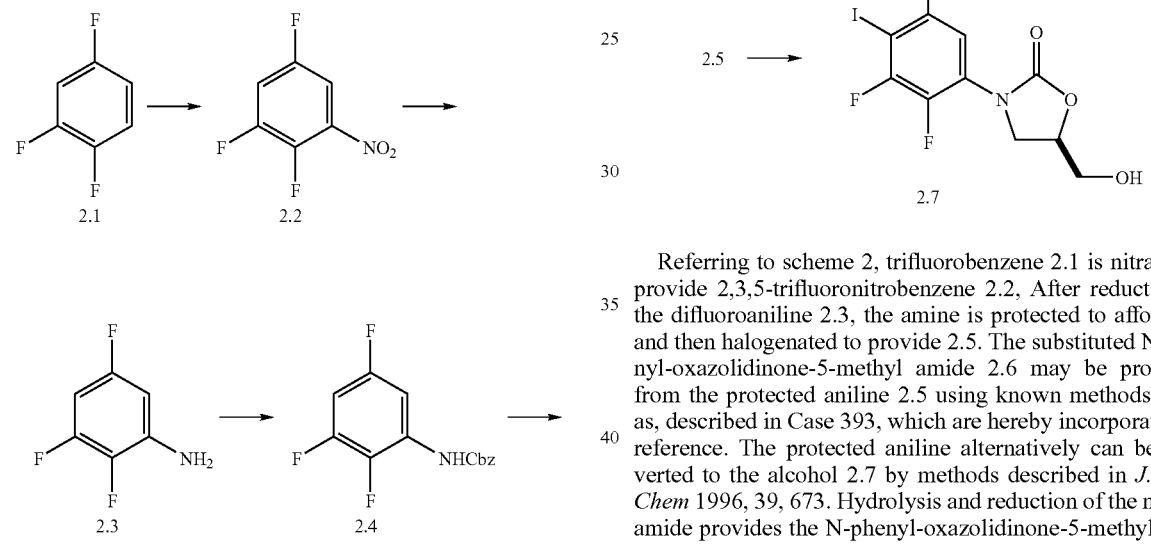

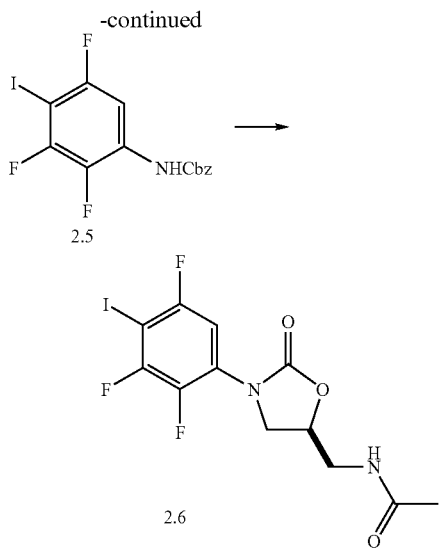

Referring to scheme 2, trifluorobenzene 2.1 is nitrated to provide 2,3,5-trifluoronitrobenzene 2.2, After reduction to the difluoroaniline 2.3, the amine is protected to afford 2.4 and then halogenated to provide 2.5. The substituted N-phenyl-oxazolidinone-5-methyl amide 2.6 may be produced from the protected aniline 2.5 using known methods, such as, described in Case 393, which are hereby incorporated by reference. The protected aniline alternatively can be converted to the alcohol 2.7 by methods described in *J. Med. Chem* 1996, 39, 673. Hydrolysis and reduction of the methyl amide provides the N-phenyl-oxazolidinone-5-methyl alcohol 2.7.

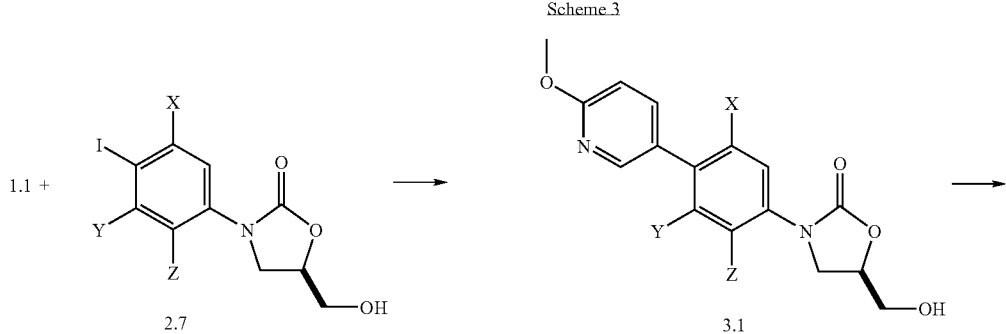

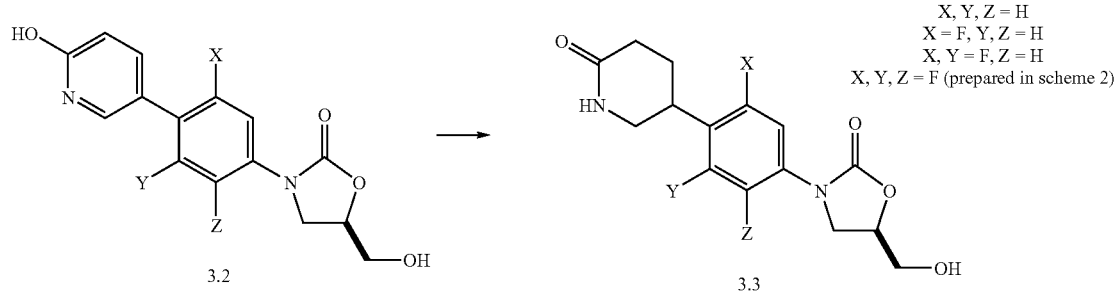
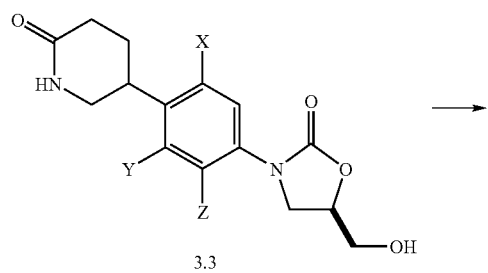
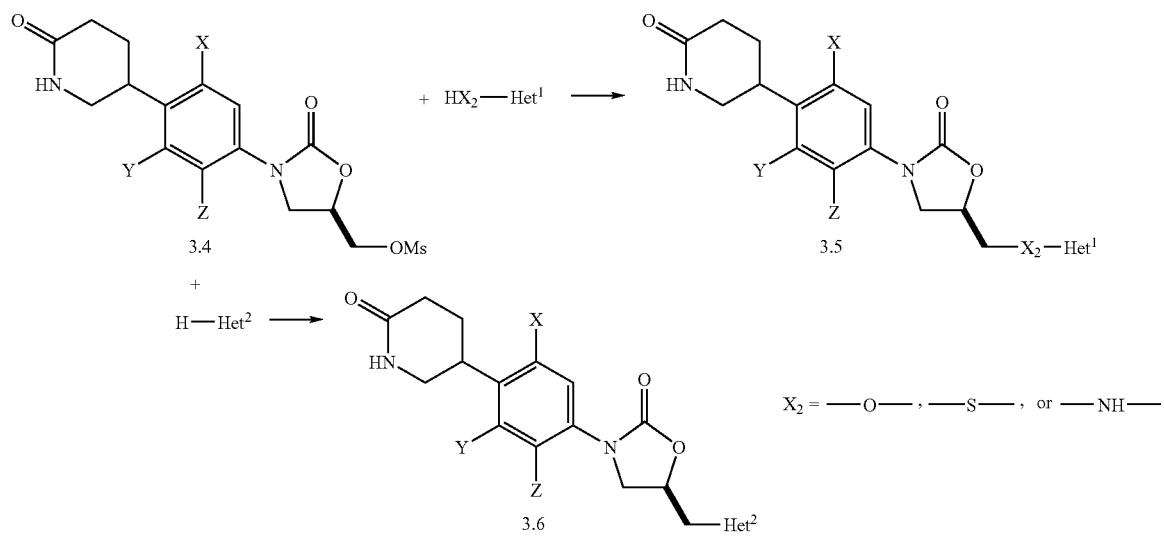

Referring scheme 3, N-phenyl-oxazolidinone-5-methyl alcohol 2.7 may be coupled to pyridine 1.1 via a Suzuki type coupling to afford 3.1 Hydrolysis of 3.1 in HCl/Dioxane affords hydroxypyridine 3.2. Reduction of the hydroxypyridine with palladium affords lactam alcohol 3.3. Reaction of alcohol 3.3 with mesyl chloride in triethylamine affords the oxopiperidinyl-phenyl-oxazolidinone-5-methylmesylate 3.4. Reaction of the mesylate 3.4 with $HX_2$-Het² or H-Het² provides the compounds 3.5 and 3.6, respectively, of formula I.

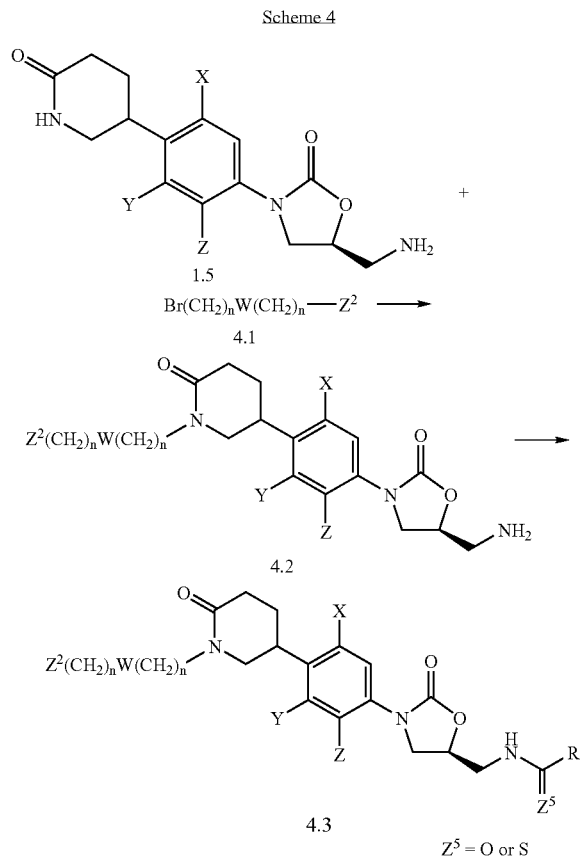

Scheme 4

Referring to scheme 4, derivatizing the lactam 1.5 includes deprotonation using a strong base such as LDA followed by alkylating the lactam nitrogen by methods known to those skilled in the art. Acylating the oxazolidinone-5-methyl amine 4.2 provides compounds 4.3 of formula I.

Suitable intermediates useful in preparating compounds of formula I and additional synthetic methods to assist in producing compounds of formula I may be found, for example, in the following publications each of which is hereby incorporated by reference.

U.S. Pat. Nos. 5,225,565; 5,182,403; 5,164,510; 5,247,090; 5,231,188; 5,565,571; 5,547,950; 5,529,998; 5,627,181; 5,843,967; 5,861,413; 5,827,857; 5,869,659; 5,952,324; 5,968,962; 5,688,792; 6,069,160; 6,239,152; 5,792,765; 4,705,799; 5,043,443; 5,652,238; 5,827,857; 5,529,998; 5,684,023; 5,627,181; 5,698,574; 6,166,056; 6,194,441; 6,110,936; 6,069,145; 6,271,383; 5,981,528; 6,051,716; 6,043,266; 6,313,307; and 5,523,403.

PCT Application and publications PCT/US93/04850, WO94/01110; PCT/US94/08904, WO95/07271; PCT/US95/02972, WO95/25106; PCT/US95/10992, WO96/13502; PCT/US96/05202, WO96/35691; PCT/US96/12766; PCT/US96/13726; PCT/US96/14135; PCT/US96/17120; PCT/US96/19149; PCT/US97/01970; PCT/US95/12751, WO96/15130, PCT/US96/00718, WO96/23788, WO98/54161, WO99/29688, WO99/03846, WO99/37641, WO99/37652, WO99/40094, WO97/30995, WO97/09328, WO01/81350, WO01/40236, WO00/21960 WO01/4022, and WO95/07271.

In some embodiments, the antibacterial compounds are prodrugs of the compounds of formula I. The expression "prodrug" denotes a derivative of a known direct acting drug, which is transformed into the active drug by an enzymatic or chemical process. Prodrugs of the compounds of formula I are prepared by modifying functional groups present on the compound in such a way that the modifications are cleaved, either in routine manipulation or in vivo, to the parent compound. Prodrugs include, but are not limited to, compounds of structure (I) wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups. See Notari, R. E., "Theory and Practice of Prodrug Kinetics," Methods in Enzymology, 112:309–323 (1985); Bodor, N., "Novel Approaches in Prodrug Design," Drugs of the Future, 6(3): 165–182 (1981), and Bundgaard, H., "Design of Prodrugs: Bioreversible-Derivatives for Various Functional Groups and Chemical Entities," in Design of Prodrugs (H. Bundgaard, ed.), Elsevier, N.Y. (1985).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

N-({(5S)-3-[3-fluoro-4-(6-oxopiperidin-3-yl)phenyl]-2-oxo-1,3-oxazolidin-5-yl}methyl)acetamide

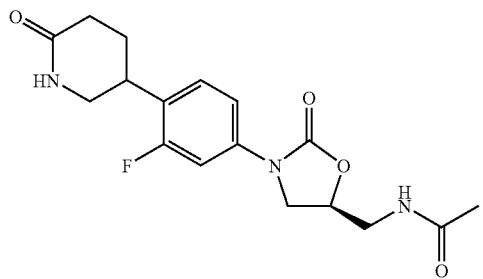

Step 1. Preparation of N-({(5S)-3-[3-fluoro-4-(6-methoxypyridin-3-yl)phenyl]-2-oxo-1,3-oxazolidin-5-yl}methyl)acetamide. To a stirred, degassed solution of 5-bromo-2-methoxypyridine (2.0 g, 11 mmol), bis(pinacolato)diboron (3.0 g, 12 mmol), and potassium acetate (3.2 g, 33 mmol) in dimethylformamide (50 mL) is added [1,1'-Bis(diphenylphosphino)-ferrocene]dichloropalladium(II), complex with dichloromethane (1:1) (0.269 g, 0.33 mmol). The solution is degassed again and heated to 85° C. for 2 hours. The solution is cooled to RT and 2M sodium carbonate (13 mL, 26 mmol), (S)-N-[[3-(3-fluoro-4-iodophenyl)-2-oxo-5-oxazolidinyl]methyl]acetamide (as described in U.S. Pat. No. 5,565,571, incorpratred herein by reference)(4.0 g, 11 mmol) and [1,1'-Bis(diphenylphosphino)-ferrocene]dichloropalladium(II), complex with dichloromethane (1:1) (0.269 g, 0.33 mmol) is added. The reaction is heated to 85° C. for 16 hours. The reaction is cooled to RT and the reaction concentrated to dryness. The residue is taken up in $CH_2Cl_2$/MeOH, absorbed onto silica and is purified on a biotage 40 M column (2 lots) with SIM using 1.5% MeOH in $CH_2Cl_2$ to afford 2.6 g (7.2 mmol, 67%) of the desired methoxypyridine compound as a pale brown solid. $^1$H-NMR (DMSO) δ: 8.35, 8.27, 7.90, 7.63, 7.58, 7.41, 6.93, 4.76, 4.17, 3.89, 3.78, 3.43, 3.43, 1.84

Step 2. Preparation of (5S)-5-(aminomethyl)-3-[3-fluoro-4-(6-hydroxypyridin-3-yl)phenyl]-1,3-oxazolidin-2-one. To a stirred mixture of the product of step 1 (0.5 g, 1.3 mmol) in dioxane (2 mL) is added concentrated hydrochloric acid (1 mL). The reaction is heated to reflux for 9 hours. The reaction is cooled to 0° C. and is poured into 100 mL of 0° C. MeOH saturated with $NH_3$ (100 mL). Silica is added and the solution is concentrated to dryness. The residue is purified on a Biotage 40 S colum with SIM using 5%–8% MeOH/$NH_3$ in $CH_2Cl_2$ to afford 0.3 g (1.0 mmol, 66%) of the desired hydroxypyridine compound. $^1$H-NMR (DMSO) δ: 7.67, 7.58, 7.53, 7.39, 6.43, 4.64, 4.08, 3.89, 2.82.

Step 3. Preparation of 5-{4-[(5S)-5-(aminomethyl)-2-oxo-1,3-oxazolidin-3-yl]-2-fluorophenyl}piperidin-2-one. The hydroxypyridine from step 2 (0.85 g, 2.8 mmol) is placed in a 250 mL parr bottle and is dissolved in trifluoroaceticacid (20 mL). To this mixture is added 10% palladium on activated carbon. The mixture is hydrogenated at 50 psi of $H_2$ and 50° C. for 4 hours. The mixture is concentrated to dryness and 50 mL of MeOH saturated with $NH_3$ is added. Silica is added and the mixture is concentrated to dryness. The residue is purified on a Biotage 40 S column with SIM using 5%–6% MeOH/$NH_4$ in $CH_2Cl_2$ to afford 0.696 g (2.3 mmol, 81% of the desired lactam. $^1$H-NMR (DMSO) δ: 7.59, 7.53, 7.39, 7.29, 4.62, 4.05, 3.85, 3.25, 2.81, 2.31, 1.90.

Step 4. Preparation of 1 N-({(5S)-3-[3-fluoro-4-(6-oxopiperidin-3-yl)phenyl]-2-oxo-1,3-oxazolidin-5-yl}methyl)acetamide. To a stirred mixture of lactam from step 3 (0.1 g, 0.35 mmol) at 0° C. in $CH_2Cl_2$ (10 mL) is added triethylamine (0.073 mL, 0.053 mmol) followed by addition of acetic anhydride (0.039 mL, 0.042 mmol). The reaction is stirred for 16 hours allowing the bath to expire. The reaction is then diluted to 50 mL with $CH_2Cl_2$ and washed with water (10 mL). The organic layer was dried ($MgSO_4$), silica is added and the mixture is concentrated to dryness. The residue is purified on a Biotage 12 M column with SIM using 2%–3% MeOH $CH_2Cl_2$ to afford 0.080 g (0.23 mmol, 67%) of the desired acetamide. $^1$H-NMR (DMSO) δ: 8.25, 7.60, 7.48, 7.40, 7.26, 4.73, 4.11, 3.73, 3.40, 3.19, 2.31, 2.04, 1.83.

Example 2

N-({(5S)-3-[3-fluoro-4-(6-oxopiperidin-3-yl)phenyl]-2-oxo-1,3-oxazolidin-5-yl}methyl)propanamide

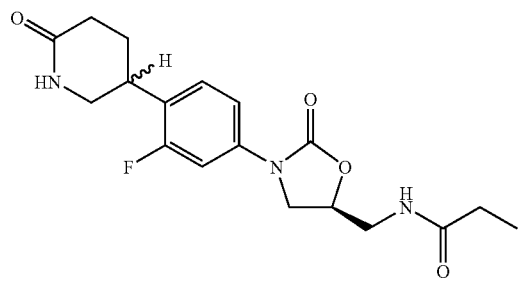

N-({(5S)-3-[3-fluoro-4-(6-oxopiperidin-3-yl)phenyl]-2-oxo-1,3-oxazolidin-5-yl}methyl)propanamide is prepared as in step 4 of Example 1 substituting propionic anhydride for acetic anhydride. $^1$H-NMR (DMSO) δ: 8.16, 7.59, 7.51, 7.39, 7.26, 4.73, 4.10, 3.74, 3.41, 3.22, 2.31, 2.09, 1.89, 0.94

Example 3

2,2-dichloro-N-({(5S)-3-[3-fluoro-4-(6-oxopiperidin-3-yl)phenyl]-2-oxo-1,3-oxazolidin-5-yl}methyl)acetamide

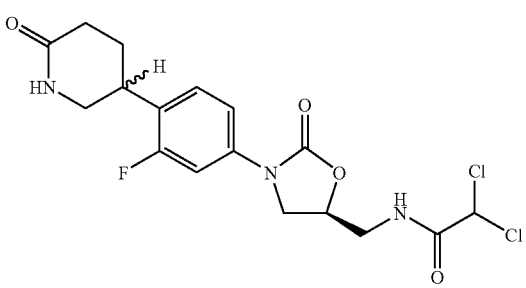

2,2-dichloro-N-({(5S)-3-[3-fluoro-4-(6-oxopiperidin-3-yl)phenyl]-2-oxo-1,3 oxazolidin-5-yl}methyl)acetamide was prepared as in step 4 of Example 1 substituting dichloroacetic anhydride for acetic anhydride. $^1$H-NMR (DMSO) δ: 7.60, 7.48, 7.39, 7.25, 6.49, 4.80, 4.13, 3.74, 3.53, 3.21, 3.17, 2.34, 2.34, 2.25, 2.05, 1.90

Example 4

2,2-difluoro-N-({(5S)-3-[3-fluoro-4-(6-oxopiperidin-3-yl)phenyl]-2-oxo-1,3-oxazolidin-5-yl}methyl)ethanethioamide

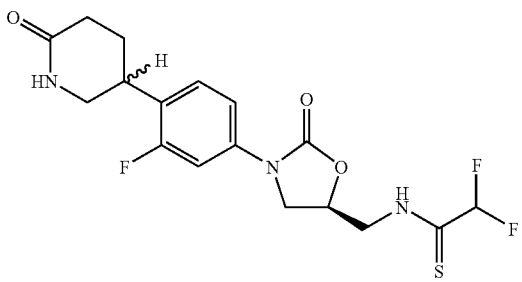

2,2-difluoro-N-({(5S)-3-[3-fluoro-4-(6-oxopiperidin-3-yl)phenyl]-2-oxo-1,3-oxazolidin-5-yl}methyl)ethanethioamide is prepared as in step 4 of Example 1 substituting O-(3,3-diphenylpropyl)difluoroethanethioate (Ref to Case 00558) for acetic anhydride. $^1$H-NMR (DMSO) δ: 11.2, 7.59, 7.48, 7.4, 7.27, 6.49, 5.0, 4.18, 3.9, 3.85, 3.22 2.26, 2.04, 1.90

Example 5

2,2-difluoro-N-({(5S)-3-[3-fluoro-4-(6-oxopiperidin-3-yl)phenyl]-2-oxo-1,3-oxazolidin-5-yl}methyl)acetamide

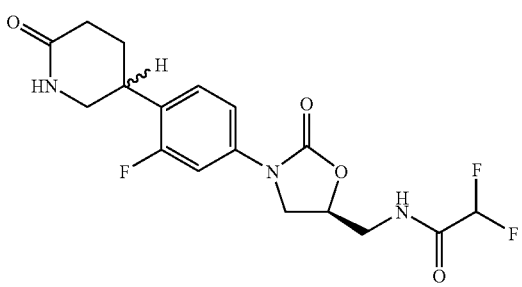

To a stirred solution of lactam from step 3, Example 1 (0.150 g, 0.049 mmol) in MeOH (7 mL) is added triethylamine (0.10 mL, 0.073 mmol) followed by dropwise addition of ethyldifluoroacetate (0.059 mL, 0.059 mmol). The reaction is stirred at RT for 16 hours. The solution is concentrated to dryness and then is diluted to 100 mL with CH$_2$Cl$_2$. The solution is washed with water (2×5 mL). The phases are separated and the organic layer is dried (MgSO$_4$). Silica is added to the solution and concentrated to dryness. The residue is purified on a Biotage 12 M column with SIM using 3% MeOH in CH$_2$Cl$_2$ to afford 0.131 g (0.34 mmol, 69%) of the desired compound. $^1$H-NMR (DMSO) δ: 11.2, 7.57, 7.48, 7.40, 7.25, 6.24, 4.8, 4.14, 3.77, 3.53, 3.22, 2.34, 2.26, 2.03, 1.89

Example 6

N-({(5S)-3-[3,5-difluoro-4-(6-oxopiperidin-3-yl)phenyl]-2-oxo-1,3-oxazolidin-5-yl}methyl)acetamide

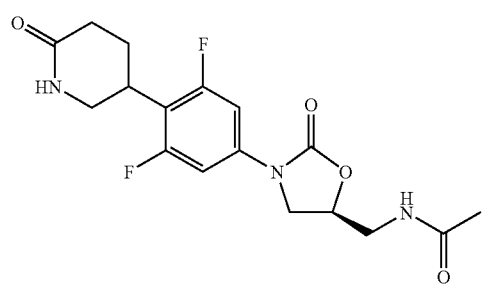

N-({(5S)-3-[3,5-difluoro-4-(6-methoxypyridin-3-yl)phenyl]-2-oxo-1,3-oxazolidin-5-yl}methyl)acetamide is prepared by the route described in Example 1 substituting N-{[(5S)-3-(3,5-difluoro-4-iodophenyl)-2-oxo-1,3-oxazolidin-5-yl]methyl}acetamide for N-({(5S)-3-[3-fluoro-4-(6-methoxypyridin-3-yl)phenyl]-2-oxo-1,3-oxazolidin-5-yl}methyl)acetamide. $^1$H-NMR (DMSO) δ: 8.25, 7.61, 7.30, 4.73, 4.10, 3.72, 3.49, 3.40, 2.30, 1.90, 1.83

Example 7

2,2-dichloro-N-({(5S)-3-[3,5-difluoro-4-(6-oxopiperidin-3-yl)phenyl]-2-oxo-1,3-oxazolidin-5-yl}methyl)acetamide

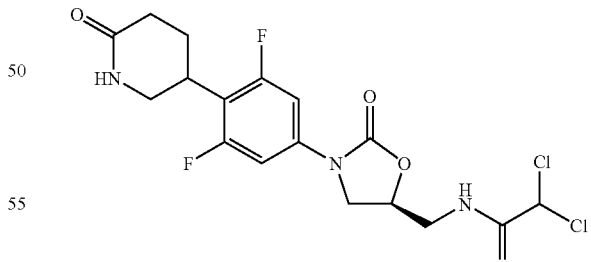

2,2-dichloro-N-({(5S)-3-[3,5-difluoro-4-(6-oxopiperidin-3-yl)phenyl]-2-oxo-1,3-oxazolidin-5-yl}methyl)acetamide is prepared as described in Example 6 substituting dichloroacetic anhydride for acetic anhydride. $^1$H-NMR (DMSO) δ: 8.97, 7.60, 7.29, 6.48, 4.82, 4.14, 3.73, 3.53, 3.37, 3.19, 23.30, 1.88

Example 8

N-({(5S)-3-[3,5-difluoro-4-(6-oxopiperidin-3-yl)phenyl]-2-oxo-1,3-oxazolidin-5-yl}methyl)-2,2-difluoroethanethioamide

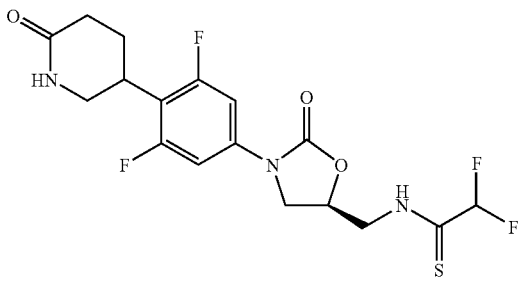

N-({(5S)-3-[3,5-difluoro-4-(6-oxopiperidin-3-yl)phenyl]-2-oxo-1,3-oxazolidin-5-yl}methyl)-2,2-difluoroethanethioamide is prepared as described in Example 4 substituting the amine prepared as an intermediate in Example 6 substituting O-(3,3-diphenylpropyl)difluoroethanethioate (Ref to Case 00558) for acetic anhydride. $^1$H-NMR (DMSO) δ: 11.20, 7.60, 6.49, 5.76, 5.04, 4.17, 3.97, 3.84, 3.34, 3.21, 2.30, 1.89

Example 9

N-({(5S)-3-[3,5-difluoro-4-(6-oxopiperidin-3-yl)phenyl]-2-oxo-1,3-oxazolidin-5-yl}methyl)-2,2-difluoroacetamide

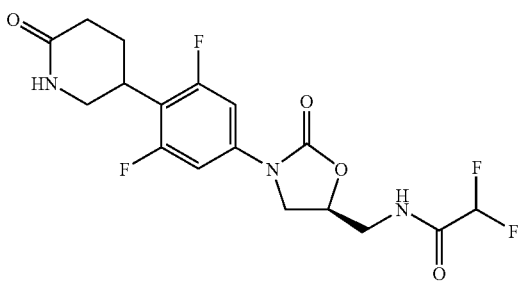

N-({(5S)-3-[3,5-difluoro-4-(6-oxopiperidin-3-yl)phenyl]-2-oxo-1,3-oxazolidin-5-yl}methyl)-2,2-difluoroacetamide is prepared as described in Example 6 substituting ethyldifluoroacetate for acetic anhydride. $^1$H-NMR (DMSO) δ: 9.20, 7.60, 7.29, 6.25, 4.82, 4.13, 3.76, 3.52, 3.33, 3.19, 3.09, 2.30, 1.89

Example 10

N-({(5S)-2-oxo-3-[4-(6-oxopiperidin-3-yl)phenyl]-1,3-oxazolidin-5-yl}methyl)acetamide

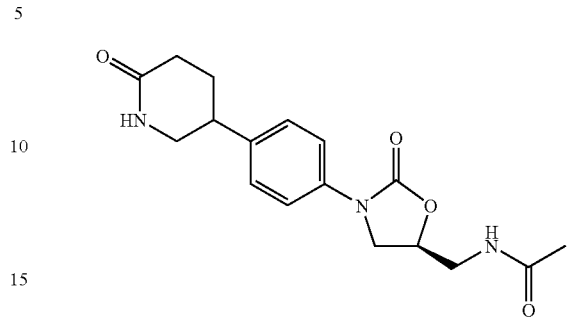

N-({(5S)-2-oxo-3-[4-(6-oxopiperidin-3-yl)phenyl]-1,3-oxazolidin-5-yl}methyl)acetamide is prepared by the route described in Example 1 substituting tert-butyl [(5S)-3-(4-iodophenyl)-2-oxo-1,3-oxazolidin-5-yl]methylcarbamate for N-{[(5S)-(3-fluoro-4-iodophenyl)-2-oxo-1,3-oxazolidin-5-yl]methyl}acetamide. $^1$H-NMR (DMSO) δ: 8.24, 7.51, 7.47, 7.33, 4.71, 4.10, 3.72, 3.40, 3.18, 3.14, 2.97, 2.28, 1.94, 1.83

Example 11

N-({(5S)-2-oxo-3-[4-(6-oxopiperidin-3-yl)phenyl]-1,3-oxazolidin-5-yl}methyl)propanamide

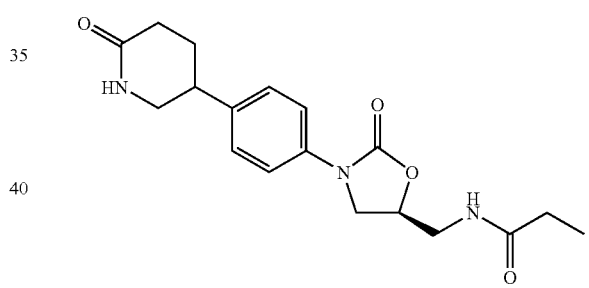

N-({(5S)-2-oxo-3-[4-(6-oxopiperidin-3-yl)phenyl]-1,3-oxazolidin-5-yl}methyl)propanamide is prepared as described in Example 10 substituting propionic anhydride for acetic anhydride. $^1$H-NMR (DMSO) δ: 8.17, 7.57, 7.46, 7.33, 4.71, 4.09, 3.73, 3.41, 3.19, 2.96, 2.25, 2.09, 1.90, 0.94.

Example 12

2,2-dichloro-N-({(5S)-2-oxo-3-[4-(6-oxopiperidin-3-yl)phenyl]-1,3-oxazolidin-5-yl}methyl)acetamide

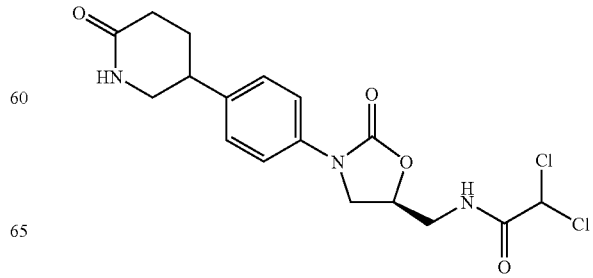

2,2-dichloro-N-({(5S)-2-oxo-3-[4-(6-oxopiperidin-3-yl)phenyl]-1,3-oxazolidin-5-yl}methyl)acetamide is prepared as described in Example 10 substituting dichloroacetic anhydride for acetic anhydride. $^1$H-NMR (DMSO) δ: 8.98, 7.57, 7.46, 7.32, 6.49, 4.79, 4.13, 3.73, 3.53, 3.02, 2.26, 1.90.

Example 13

2,2-difluoro-N-({(5S)-2-oxo-3-[4-(6-oxopiperidin-3-yl)phenyl]-1,3-oxazolidin-5-yl}methyl)ethanethioamide

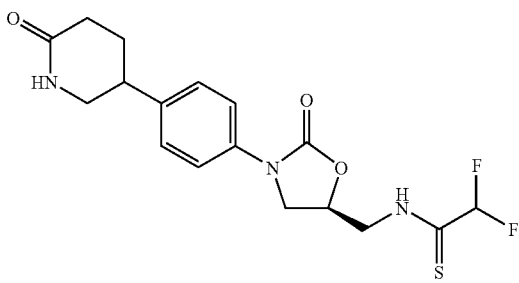

2,2-difluoro-N-({(5S)-2-oxo-3-[4-(6-oxopiperidin-3-yl)phenyl]-1,3-oxazolidin-5-yl}methyl)ethanethioamide is prepared as described in Example 10 substituting O-(3,3-diphenylpropyl)difluoroethanethioate for acetic anhydride. $^1$H-NMR (DMSO) δ: 11.3, 7.58, 7.48, 7.34, 6.50, 5.01, 4.18, 3.97, 3.85, 3.39, 3.23, 3.01, 2.25, 1.90

Example 14

2,2-difluoro-N-({(5S)-2-oxo-3-[4-(6-oxopiperidin-3-yl)phenyl]-1,3-oxazolidin-5-yl}methyl)ethanethioamide

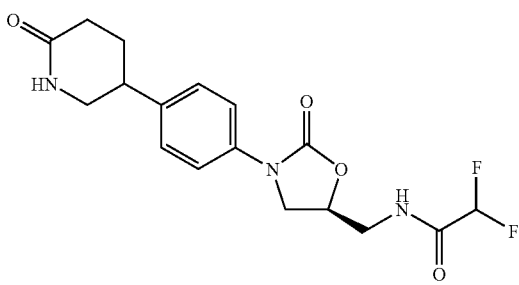

2,2-difluoro-N-({(5S)-2-oxo-3-[4-(6-oxopiperidin-3-yl)phenyl]-1,3-oxazolidin-5-yl}methyl)ethanethioamide is prepared as described in Example 10 substituting ethyldifluoroacetate for acetic anhydride. $^1$H-NMR (DMSO) δ: 11.3, 7.58, 7.47, 7.34, 6.25, 4.78, 4.14, 3.77, 3.52, 3.35, 3.19, 2.96, 2.26, 1.90

Example 15

({(5S)-3-[4-(1-methyl-6-oxopiperidin-3-yl)phenyl]-2-oxo-1,3-oxazolidin-5-yl}methyl)acetamide

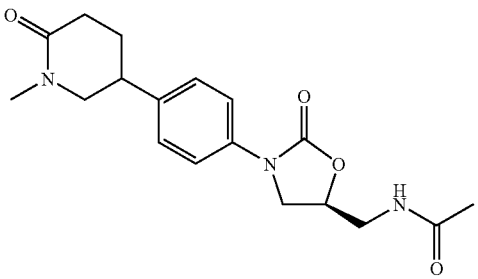

Step 1. Preparation of N-({(5S)-3-[4-(6-methoxypyridin-3-yl)phenyl]-2-oxo-1,3-oxazolidin-5-yl}methyl)acetamide.

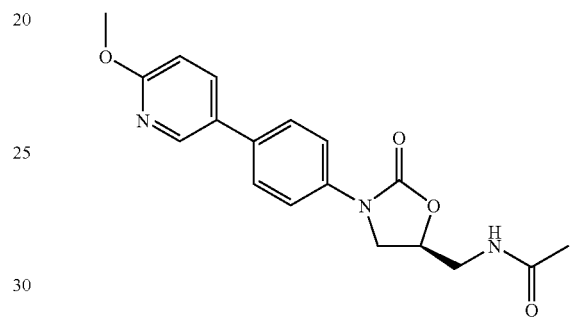

To a stirred, degassed solution of 5-bromo-2-methoxypyridine (2.0 g, 1.1 mmol), bis(pinacolato)diboron (3.0 g, 1.2 mmol), and potassium acetate (3.2 g, 3.3 mmol) in dimethylformamide (50 mL) is added [1,1'-bis(diphenylphosphino)-ferrocene]dichloropalladium(II), complex with dichloromethane (1:1) (0.269 g, 0.33 mmol). The solution is degassed again and heated to 85° C. for 2 hours. The solution is cooled to RT and 2M sodium carbonate (13 mL, 26 mmol), (S)-N-[[3-(3-fluoro-4-iodophenyl)-2-oxo-5-oxazolidinyl]methyl]acetamide (as described in U.S. Pat. No. 5,565,571)(4.0 g, 1.1 mmol) and [1,1'-bis(diphenylphosphino)-ferrocene]dichloropalladium(II), complex with dichloromethane (1:1) (0.269 g, 0.33 mmol) is added. The reaction is heated to 85° C. for 16 hours. The reaction is cooled to RT and the reaction concentrated to dryness. The residue is taken up in CH$_2$Cl$_2$/MeOH, absorbed onto silica and is purified on a biotage 40 M column (2 lots) with SIM using 1.5% MeOH in CH$_2$Cl$_2$ to afford 1.7 g (5.1 mmol, 47%) of the desired methoxypyridine compound as a pale brown solid. $^1$H-NMR (DMSO) δ: 8.49, 8.27, 8.01, 7.65, 6.90, 4.74, 4.16, 3.89, 3.78, 3.43, 1.84

Step 2. N-({(5S)-3-[4-(1-methyl-6-oxo-1,6-dihydropyridin-3-yl)phenyl]-2-oxo-1,3-oxazolidin-5-yl}methyl)acetamide

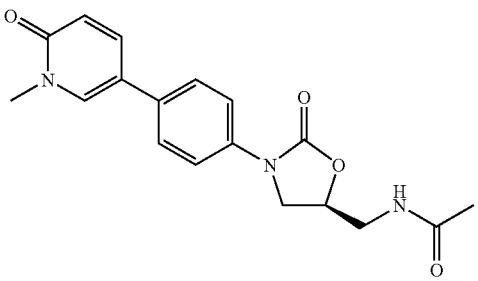

To a stirred anhydrous THF (10 mL) mixture of N-({(5S)-3-[4-(6-methoxypyridin-3-yl)phenyl]-2-oxo-1,3-oxazolidin-5-yl}methyl)acetamide (0.10 g, 0.29 mmol) in a sealed tube, is added potassium carbonate (0.04 g, 0.58 mmol) and methyl iodide (0.1 mL, 1.7 mmol). The mixture is heated to 85° C. for 16 hours. The reaction is cooled to RT and diluted to 100 mL with CH$_2$Cl$_2$. The K$_2$CO$_3$ is filtered. The solution is concentrated to dryness, dissolved in MeOH (20 mL) and treated with saturated Na$_2$S$_2$O$_3$. The solution is concentrated to dryness on silica. The residue is loaded onto a SIM and purified on a Biotage 12M column with 2–4% MeOH in CH$_2$Cl$_2$ to yield the desired compound (0.23 g, 53%). $^1$H-NMR (DMSO) δ: 8.26, 8.12, 7.82, 7.59, 6.47, 4.73, 4.14, 3.77, 3.50, 3.42, 1.84

Step 3. N-({(5S)-3-[4-(1-methyl-6-oxopiperidin-3-yl)phenyl]-2-oxo-1,3-oxazolidin-5-yl}methyl)acetamide

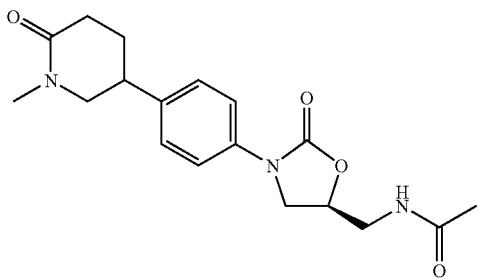

To a mixture of N-({(5S)-3-[4-(1-methyl-6-oxo-1,6-dihydropyridin-3-yl)phenyl]-2-oxo-1,3-oxazolidin-5-yl}methyl)acetamide (0.179 g. 0.52 mmol) in 20 mL of MeOH is added 0.05 g of 10% palladium on activated charcoal. The mixture is hydrogenated at 50 psi for 16 hours. The reaction mixture is filtered through celite, silica is added and the mixture is concentrated to dryness. The residue is loaded onto a SIM and purified on a Biotage 12S column with 2% MeOH in CH$_2$Cl$_2$ to yield the desired compound (0.175 g, 96%). $^1$H-NMR (DMSO) δ: 8.25, 7.41, 4.70, 4.10, 3.74, 3.39, 3.17, 2.83, 2.32, 2.01, 1.83

Example 16

N-({(5S)-3-[3-fluoro-4-(2-oxopiperidin-4-yl)phenyl]-2-oxo-1,3-oxazolidin-5-yl}methyl)acetamide

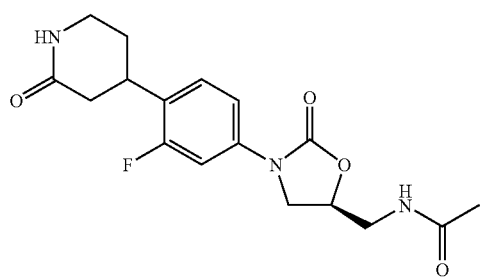

Step 1. Preparation of N-({(5S)-3-[3-fluoro-4-(2-methoxypyridin-4-yl)phenyl]-2-oxo-1,3-oxazolidin-5-yl}methyl)acetamide.

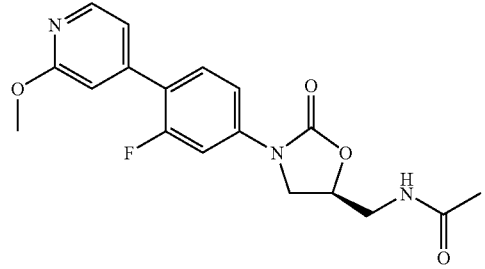

To a stirred, degassed solution of N-{[(5S)-3-(3-fluoro-4-iodophenyl)-2-oxo-1,3-oxazolidin-5-yl]methyl}acetamide (2.0 g, 5.3 mmol), bis(pinacolato)diboron (1.5 g, 5.8 mmol), and potassium acetate (1.5 g, 1.6 mmol) in dimethylformamide (50 mL) is added [1,1'-bis(diphenylphosphino)-ferrocene]dichloropalladium(II), complex with dichloromethane (1:1) (0.130 g, 0.16 mmol). The solution is degassed again and heated to 85° C. for 2 hours. The solution is cooled to RT and 2M sodium carbonate (13 mL, 26 mmol) 4-iodo-2-methoxypyridine (*J. Het Chem.* 1985, 22, 145, and *Org. Prep and Proceed Int.* 1994, 26, 696. (1.2 g, 5.3 mmol) and [1,1'-bis(diphenylphosphino)-ferrocene]dichloropalladium(II), complex with dichloromethane (1:1) (0.130 g, 0.16 mmol) is added. The reaction is heated to 85° C. for 16 hours. The reaction is cooled to RT and the reaction concentrated to dryness. The residue is taken up in CH$_2$Cl$_2$/MeOH, absorbed onto silica and is purified on a biotage 40 M column (2 lots) with SIM using 1.5% MeOH in CH$_2$Cl$_2$ to afford 0.8 g (2.2 mmol, 42%) of the desired methoxypyridine compound as a pale brown solid. $^1$H-NMR (DMSO) δ: 8.25, 7.69, 7.62, 7.45, 7.18, 6.98, 4.77, 4.17, 3.89, 3.79, 3.43, 1.84

Step 2. Preparation of (5S)-5-(aminomethyl)-3-[3-fluoro-4-(2-hydroxypyridin-4-yl)phenyl]-1,3-oxazolidin-2-one.

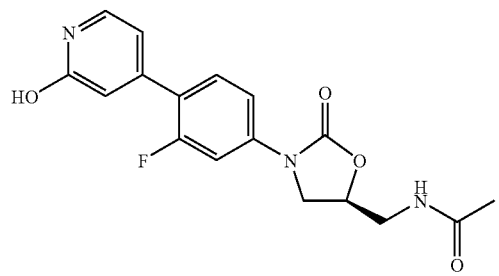

To a stirred mixture of the product of step 2 (0.2 g, 0.5 mmol) in dioxane (3 mL) is added concentrated hydrochloric acid (0.5 mL). The reaction is heated to reflux for 16 hours. The reaction is cooled to 0° C. and is poured into 100 mL of 0° C. MeOH saturated with NH$_3$ (100 mL). Silica is added and the solution is concentrated to dryness. The residue is purified on a Biotage 40 S colum with SIM using 5%–8% MeOH/NH$_3$ in CH$_2$Cl$_2$ to afford 0.12 g (1.0 mmol, 84%) of the desired hydroxypyridine compound: $^1$H-NMR (DMSO) δ: 10.15, 8.25, 8.21, 8.15, 7.63, 7.59, 7.43, 7.32, 4.76, 4.17, 3.78, 3.43, 1.84

Step 3. Preparation of 4-{4-[(5S)-5-(aminomethyl)-2-oxo-1, 3-oxazolidin-3-yl]-2-fluorophenyl}piperidin-2-one.

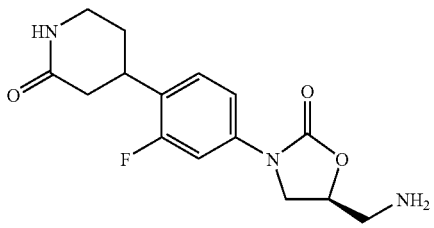

The hydroxypyridine from step 3 (0.650 g, 2.0 mmol) is placed in a 250 mL parr bottle and is dissolved in trifluoroaceticacid (20 mL). To this mixture is added 10% palladium on activated carbon (0.600 g). The mixture is hydrogenated at 50 psi of $H_2$ and 50° C. for 4 hours. The mixture is concentrated to dryness and 50 mL of MeOH saturated with $NH_3$ is added. Silica is added and the mixture is concentrated to dryness. The residue is purified on a Biotage 40 S column with SIM using 5%–6% MeOH/$NH_4$ in $CH_2Cl_2$ to afford 0.469 g (1.5 mmol, 72% of the desired lactam. $^1$H-NMR (DMSO) δ: 8.25, 7.61, 7.48, 7.37, 7.28, 4.75, 4.11, 3.73, 3.28, 1.88

Step 4. Preparation of N-({(5S)-3-[3-fluoro-4-(2-oxopiperidin-4-yl)phenyl]-2-oxo-1,3-oxazolidin-5-yl}methyl)acetamide.

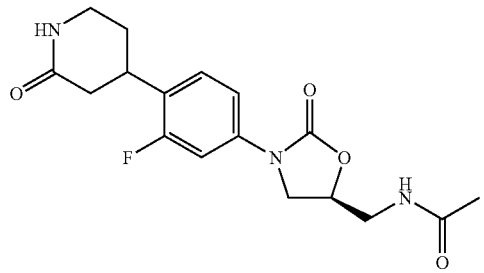

To a stirred mixture of lactam from step 4 (0.1 g, 0.35 mmol) at 0° C. in $CH_2Cl_2$ (10 mL) is added triethylamine (0.073 mL, 0.053 mmol) followed by addition of acetic anhydride (0.039 mL, 0.042 mmol). The reaction is stirred for 16 hours allowing the bath to expire. The reaction is then diluted to 50 mL with $CH_2Cl_2$ and washed with water (10 mL). The organic layer was dried (MgSO$_4$), silica is added and the mixture is concentrated to dryness. The residue is purified on a Biotage 12 M column with SIM using 2%–3% MeOH $CH_2Cl_2$ to afford 0.080 g (0.23 mmol, 67%) of the desired acetamide. $^1$H-NMR (DMSO) δ: 8.25, 7.61, 7.48, 7.37, 7.28, 4.75, 4.11, 3.73, 3.28, 1.88, 1.83

Example 17

N-({(5S)-3-[3-fluoro-4-(2-oxopiperidin-4-yl)phenyl]-2-oxo-1,3-oxazolidin-5-yl}methyl)propanamide

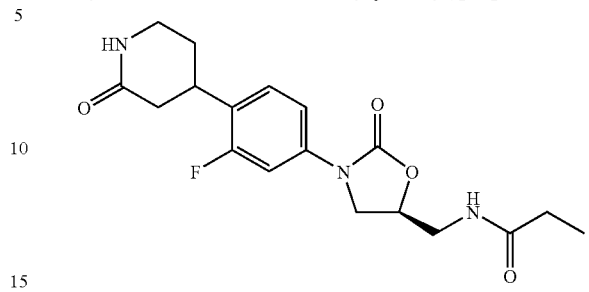

N-({(5S)-3-[3-fluoro-4-(2-oxopiperidin-4-yl)phenyl]-2-oxo-1,3-oxazolidin-5-yl}methyl)propanamide is prepared as described in Step 4 Example 16 substituting propionic anhydride for acetic anhydride. $^1$H-NMR (DMSO) δ: 8.16, 7.60, 7.47, 7.36, 7.29, 4.11, 3.74, 3.74, 3.42, 3.28, 2.32, 2.08, 1.87, 0.95

Example 18

2,2-difluoro-N-({(5S)-3-[3-fluoro-4-(2-oxopiperidin-4-yl)phenyl]-2-oxo-1,3-oxazolidin-5-yl}methyl)ethanethioamide

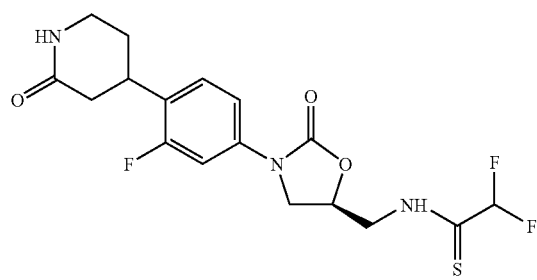

2,2-difluoro-N-({(5S)-3-[3-fluoro-4-(2-oxopiperidin-4-yl)phenyl]-2-oxo-1,3-oxazolidin-5-yl}methyl)ethanethioamide is prepared as in step 4 of Example 16 substituting O-(3,3-diphenylpropyl)difluoroethanethioate (Ref to Case 00558) for acetic anhydride. $^1$H-NMR (DMSO) δ: 11.12, 7.57, 7.48, 7.30, 6.50, 5.02, 4.18, 3.97, 3.87, 3.20, 3.02, 2.31, 2.28, 1.87

Example 19

N-({(5S)-3-[3,5-difluoro-4-(2-oxopiperidin-4-yl)phenyl]-2-oxo-1,3-oxazolidin-5-yl}methyl)acetamide

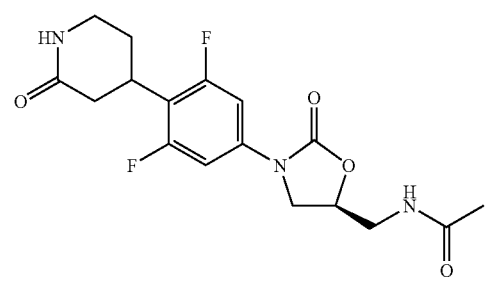

N-({(5S)-3-[3,5-difluoro-4-(2-oxopiperidin-4-yl)phenyl]-2-oxo-1,3-oxazolidin-5-yl}methyl)acetamide is prepared as in the route described in Example 16 substituting N-{[(5S)-3-(3,5-difluoro-4-iodophenyl)-2-oxo-1,3-oxazolidin-5-yl]methyl}acetamide for 1 N-{[(5S)-3-(3-fluoro-4-iodophenyl)-2-oxo-1,3-oxazolidin-5-yl]methyl}acetamide.
$^1$H-NMR (CDCl$_3$) δ: 7.13, 6.09, 5.8, 4.79, 4.01, 3.74, 3.68, 3.44, 2.75, 2.62, 2.31, 2.02, 1.94

Example 20

N-({(5S)-3-[3,5-difluoro-4-(2-oxopiperidin-4-yl)phenyl]-2-oxo-1,3-oxazolidin-5-yl}methyl)propanamide

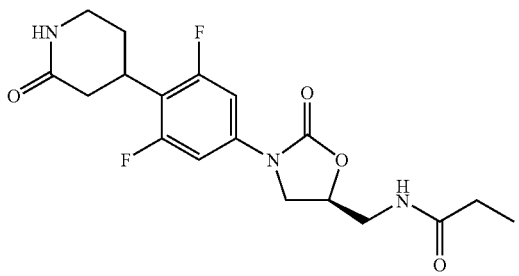

N-({(5S)-3-[3,5-difluoro-4-(2-oxopiperidin-4-yl)phenyl]-2-oxo-1,3-oxazolidin-5-yl}methyl)propanamide is prepared as in Example 19 substituting propionic anhydride for acetic anhydride

Example 21

N-({(5S)-3-[3,5-difluoro-4-(2-oxopiperidin-4-yl)phenyl]-2-oxo-1,3-oxazolidin-5-yl}methyl)-2,2-difluoroethanethioamide

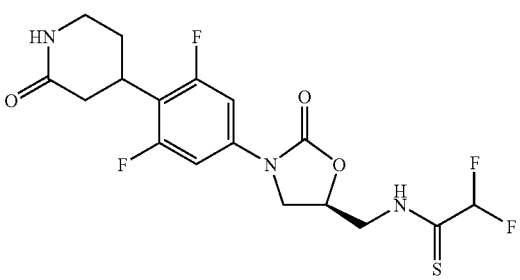

N-({(5S)-3-[3,5-difluoro-4-(2-oxopiperidin-4-yl)phenyl]-2-oxo-1,3-oxazolidin-5-yl}methyl)-2,2-difluoroethanethioamide is prepared as in Example 19 substituting O-(3,3-diphenylpropyl)difluoroethanethioate (Ref to Case 00558) for acetic anhydride.

Example 22

N-({(5S)-2-oxo-3-[4-(2-oxopiperidin-4-yl)phenyl]-1,3-oxazolidin-5-yl}methyl)acetamide

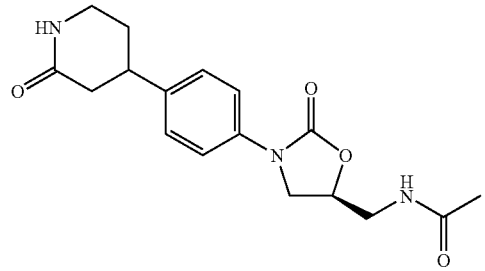

N-({(5S)-2-oxo-3-[4-(2-oxopiperidin-4-yl)phenyl]-1,3-oxazolidin-5-yl}methyl)acetamide is prepared as described in the route described in Example 16 substituting tert-butyl [(5S)-3-(4-iodophenyl)-2-oxo-1,3-oxazolidin-5-yl]methylcarbamate for N-{[(5S)-3-(3-fluoro-4-iodophenyl)-2-oxo-1,3-oxazolidin-5-yl]methyl}acetamide. $^1$H-NMR (DMSO) δ: 8.25, 7.55, 7.47, 7.30, 4.70, 4.10, 3.73, 3.40, 3.17, 3.02, 2.31, 1.87, 1.83

Example 23

2,2-difluoro-N-({(5S)-2-oxo-3-[4-(2-oxopiperidin-4-yl)phenyl]-1,3-oxazolidin-5-yl}methyl)ethanethioamide

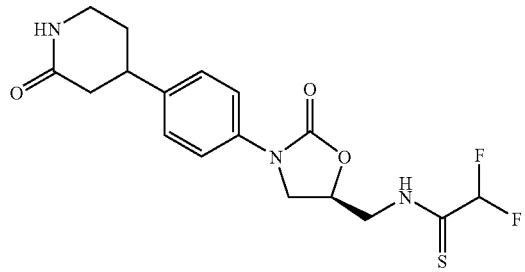

2,2-difluoro-N-({(5S)-2-oxo-3-[4-(2-oxopiperidin-4-yl)phenyl]-1,3-oxazolidin-5-yl}methyl)ethanethioamide is prepared as described in step 22 substituting O-(3,3-diphenylpropyl)difluoroethanethioate (Ref to Case 00558) for acetic anhydride., 3.22, 2.38, 1.89,
$^1$H-NMR (DMSO) δ: 11.12, 7.31, 7.28, 6.50, 5.04, 4.18, 3.96, 3.84, 3.56, 3.30

Example 24

N-({(5S)-2-oxo-3-[4-(2-oxopiperidin-4-yl)phenyl]-1,3-oxazolidin-5-yl}methyl)propanamide

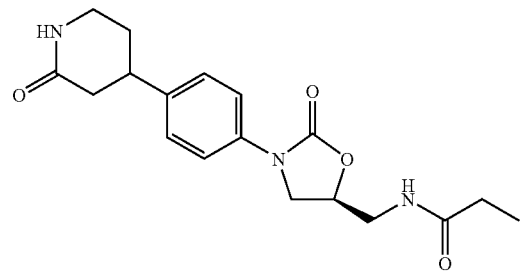

N-({(5S)-2-oxo-3-[4-(2-oxopiperidin-4-yl)phenyl]-1,3-oxazolidin-5-yl}methyl)propanamide is prepared as described in Example 22 substituting propionic anhydride for acetic anhydride. ¹H-NMR (DMSO) δ: 8.16, 7.64, 7.31, 7.27, 4.74, 4.10, 3.72, 3.41, 3.22, 2.38, 2.10, 1.89, 0.95

Example 25

N-({(5S)-3-[4-(1-methyl-2-oxopiperidin-4-yl)phenyl]-2-oxo-1,3-oxazolidin-5-yl}methyl)acetamide

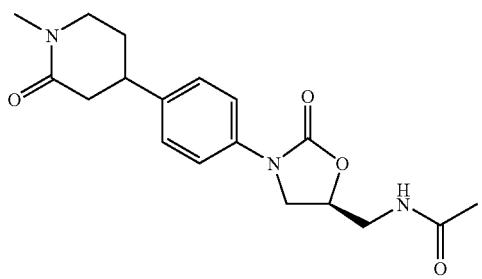

Step 1. Preparation of N-({(5S)-3-[4-(2-methoxypyridin-4-yl)phenyl]-2-oxo-1,3-oxazolidin-5-yl}methyl)acetamide

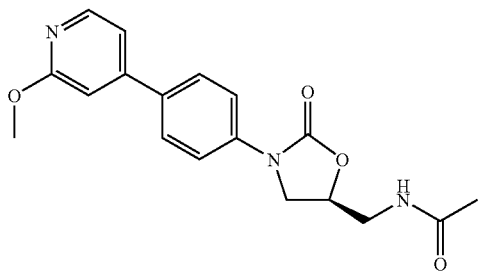

To a stirred, degassed solution of N-{[(5S)-3-(4-iodophenyl)-2-oxo-1,3-oxazolidin-5-yl]methyl}acetamide (2.0 g, 8.5 mmol), bis(pinacolato)diboron (2.4 g, 9.4 mmol), and potassium acetate (2.4 g, 25 mmol) in dimethylformamide (50 mL) is added [1,1'-bis(diphenylphosphino)-ferrocene]dichloropalladium(II), complex with dichloromethane (1:1) (0.204 g, 0.25 mmol). The solution is degassed again and heated to 85° C. for 2 hours. The solution is cooled to RT and 2M sodium carbonate (21 mL, 43 mmol) 4-iodo-2-methoxypyridine (*J. Het. Chem.* 1985, 22, 145 and *Org. Prep and Proceed Int.* 1994, 26, 696). (2.0 g, 8.5 mmol) and [1,1'-bis(diphenylphosphino)-ferrocene]dichloropalladium(II), complex with dichloromethane (1:1) (0.204 g, 0.25 mmol) is added. The reaction is heated to 85° C. for 16 hours. The reaction is cooled to RT and the reaction concentrated to dryness. The residue is taken up in CH₂Cl₂/MeOH, absorbed onto silica and is purified on a biotage 40 M column (2 lots) with SIM using 1.5% MeOH in CH₂Cl₂ to afford 1.4 g (2.2 mmol, 50%) of the desired methoxypyridine compound as a pale brown solid. ¹H-NMR (DMSO) δ: 8.27, 7.85, 7.66, 7.32, 7.12, 4.75, 4.17, 3.80, 3.43, 1.83

Step 2. Preparation of N-({(5S)-3-[4-(1-methyl-2-oxo-1,2-dihydropyridin-4-yl)phenyl]-2-oxo-1,3-oxazolidin-5-yl}methyl)acetamide.

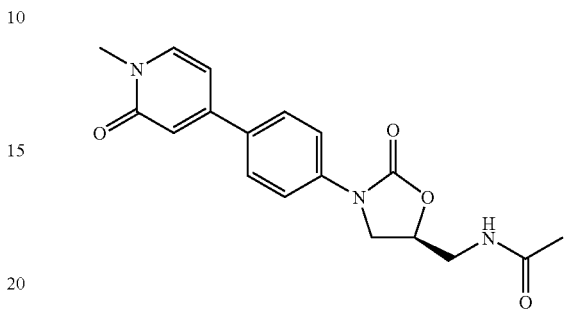

To a stirred anhydrous THF (10 mL) mixture of N-({(5S)-3-[4-(2-methoxypyridin-4-yl)phenyl]-2-oxo-1,3-oxazolidin-5-yl}methyl)acetamide (0.667 g, 1.95 mmol) in a sealed tube, is added potassium carbonate (0.807 g, 6.0 mmol) and methyl iodide (1 mL, 17 mmol). The mixture is heated to 85° C. for 16 hours. The reaction is cooled to RT and diluted to 300 mL with CH₂Cl₂. The K₂CO₃ is filtered. The solution is concentrated to dryness, dissolved in MeOH (20 mL) and treated with saturated Na₂S₂O₃. The solution is concentrated to dryness on silica. The residue is loaded onto a SIM and purified on a Biotage 12M column with 2–4% MeOH in CH₂Cl₂ to yield the desired compound (0.460 g, 69%). ¹H-NMR (DMSO) δ: 8.26, 7.77, 7.64, 6.68, 6.60, 4.74, 4.17, 3.78, 3.43, 1.83

Step 3. N-({(5S)-3-[4-(1-methyl-2-oxopiperidin-4-yl)phenyl]-2-oxo-1,3-oxazolidin-5-yl}methyl)acetamide.

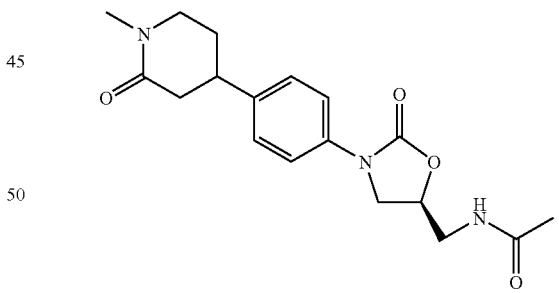

To a mixture of N-({(5S)-3-[4-(1-methyl-2-oxo-1,2-dihydropyridin-4-yl)phenyl]-2-oxo-1,3-oxazolidin-5-yl}methyl)acetamide (0.170 g. 0.49 mmol) in 20 mL of MeOH is added 0.05 g of 10% palladium on activated charcoal. The mixture is hydrogenated at 50 psi for 16 hours. The reaction mixture is filtered through celite, silica is added and the mixture is concentrated to dryness. The residue is loaded onto a SIM and purified on a Biotage 12S column with 2% MeOH in CH₂Cl₂ to yield the desired compound (0.165 g, 96%). ¹H-NMR (DMSO) δ: 8.25, 7.48, 7.28, 4.70, 4.10, 3.72, 3.40, 3.29, 3.05, 2.84, 2.39, 1.93, 1.83.

Example 26

5-{2,6-difluoro-4-[(5R)-2-oxo-5-(1H-1,2,3-triazol-1-ylmethyl)-1,3-oxazolidin-3-yl]phenyl}piperidin-2-one

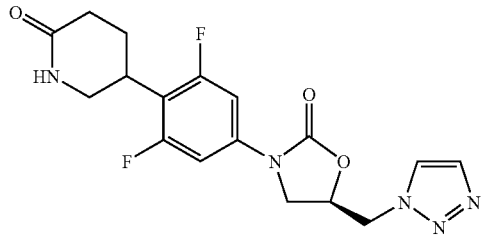

Step 1. Preparation of N'-[(1E)-2,2-dichloroethylidene]-4-methylbenzenesulfonohydrazide

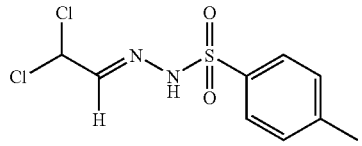

To 50 mL of propionic acid is added p-toluenesulfonhydrazide (5.0 g, 27 mmol). The mixture is cooled to 0° C. Dichloroacetaldehyde (3.0 g, 27 mmol) is added portionwise over 1 minute. The reaction is stirred at 0° C. for 1.5 hours. The mixture is filtered and washed extensively with toluene. The washed residue is dried at room temperature under house vacuum to yield (3.7 g, 50%). $^1$H-NMR (DMSO) δ: 8.19, 7.82, 7.36, 7.21, 6.12, 2.46

Step 2. Preparation of 5-{2,6-difluoro-4-[(5R)-2-oxo-5-(1H-1,2,3-triazol-1-ylmethyl)-1,3-oxazolidin-3-yl]phenyl}piperidin-2-one.

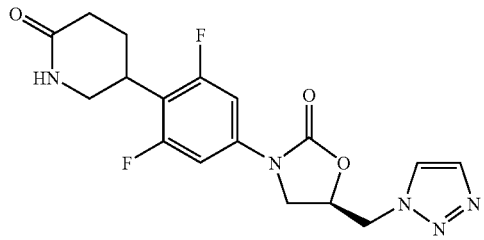

5-{4-[(5S)-5-(aminomethyl)-2-oxo-1,3-oxazolidin-3-yl]-2,6-difluorophenyl}piperidin-2-one (0.1 g, 0.31 mmol) (prepared by the route described in Example 1, substituting N-{[(5S)-3-(3,5-difluoro-4-iodophenyl)-2-oxo-1,3-oxazolidin-5-yl]methyl}acetamide) is dissolved in MeOH (2 mL). To this mixture is added Et$_3$N (0.125 ml, 0.9 mmol) and N'-[(1E)-2,2-dichloroethylidene]-4-methylbenzenesulfonohydrazide (0.17 g, 0.6 mmol)(Prepared in Example 26 step 1). The reaction is stirred at 0° C. to RT for 16 hours. The mixture was concentrated to dryness, reconstituted in CH$_2$Cl$_2$ (125 mL) and extracted with H$_2$O. The organic layer was dried (MgSO$_4$), loaded onto a SIM and purified on a Biotage 12M column to yield (0.033 g, 30%). $^1$H-NMR (DMSO) δ: 8.17, 7.77, 7.61, 7.25, 5.16, 4.83, 4.21, 3.87, 3.28, 3.18, 2.29, 1.86

Example 27

MIC Test Method

The in vitro MICs of test compounds were determined by a standard agar dilution method. A stock drug solution of each analog was prepared in the preferred solvent, usually DMSO:H$_2$O (1:3). Serial 2-fold dilutions of each sample are made using 1.0 ml aliquots of sterile distilled water. To each 1.0 ml aliquot of drug was added 9 ml of molten Mueller Hinton gar medium. The drug-supplemented agar was mixed, poured into 15×100 mm petri dishes, and allowed to solidify and dry prior to inoculation.

Vial of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension was made in TSB. The plates containing the drug supplemented agar are inoculated with a 0.001 ml drop of the cell suspension using a Steers replicator, yielding approximately 10$^4$ to 10$^5$ cells per spot. The plates are incubated overnight at 35° C.

Following incubation the Minimum Inhibitory Concentration (MIC µg/ml), the lowest concentration of the drug that inhibits visible growth of the organism, was read and recorded. The data is shown in Table I.

TABLE 1

| Example No. | Saur 9213 MIC: µg/ml |
| --- | --- |
| 1 | 4 |
| 2 | 4 |
| 3 | 4 |
| 4 | 1 |
| 5 | 4 |
| 6 | 4 |
| 7 | 2 |
| 8 | 1 |
| 9 | 4 |
| 10 | 8 |
| 11 | 8 |
| 12 | 4 |
| 13 | 2 |
| 14 | 4 |
| 15 | 8 |
| 16 | 2 |
| 17 | 4 |
| 18 | 1 |
| 19 | 4 |
| 20 | 8 |
| 21 | 2 |
| 22 | 4 |
| 23 | 1 |
| 24 | 8 |
| 25 | 4 |
| 26 | 2 |

What is claimed is:

1. A compound of formula I

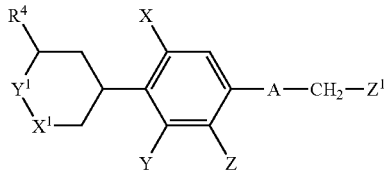

or a pharmaceutically acceptable salt thereof wherein:

A is

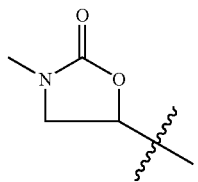

$X^1$ and $Y^1$ together form the group —C(=O)N($R^5$)— wherein $X^1$ is $NR^5$ and $Y^1$ is C(=O)

$Z^1$ is
  (a) NHC(=O)$R^1$, or
  (b) NHC(=S)$R^1$;

$R^1$ is
  (a) $NH_2$,
  (b) $NHC_{1-4}$alkyl,
  (c) $C_{1-4}$alkyl,
  (d) $C_{2-4}$alkenyl,
  (e) —$CH_2$C(=O)$C_{1-4}$alkyl,
  (f) $OC_{1-4}$alkyl,
  (g) $SC_{1-4}$alkyl, or
  (h) $C_{3-6}$cycloalkyl;

Each X, Y, and Z is independently selected from
  (a) H,
  (b) Cl,
  (c) F, or
  (d) $CH_3$ $R^4$ is
  (a) H,
  (b) $C_{1-4}$alkyl,
  (c) $OC_{1-4}$alkyl,
  (d) $SC_{1-4}$alkyl, or
  (e) $NHC_{1-4}$alkyl;

$R^5$ is
  (a) H,
  (b) $C_{1-4}$alkyl, or
  (c) —$(CH_2)_n$—$W_1$—$(CH_2)_n$-$Z^3$;

$W_1$ is
  (a) —$CH_2$—,
  (b) —CH=CH—,
  (c) —C≡C—, or (d)
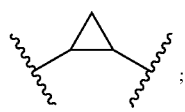

$Z^3$ is

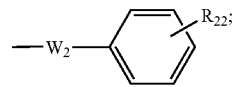

$W_2$ is
  (a) —O—,
  (b) —N($R_{25}$)—, or
  (c) —C(=O)—N($R_{25}$)—, wherein either the carbon or the nitrogen atom of the amide may be bound to a carbon atom of the phenyl ring of $Z^3$;

$R_{22}$ is $(CH_2)_tNR_{23}R_{24}$, H, halo, $C_{1-4}$alkyl, —CN, —OH, —O—$C_{1-4}$alkyl, —S(O)$_u$$C_{1-4}$alkyl, and —C(=O)$NH_2$ $R_{23}$ is H or $C_{1-4}$ alkyl;

$R_{24}$ is is H, $C_{1-4}$ alkyl, —S(O)$_2$—$C_{1-4}$alkyl, —C(=O)—$C_{1-4}$ alkyl, —C(=NH)—$NH_2$, —C(=O)—C(H$R_{26}$)—$NR_{27}R_{28}$;

$R_{25}$ is H or $C_{1-4}$ alkyl;

$R_{26}$ is H, $C_{1-4}$ alkyl which can be optionally substituted by —OH, —$NH_2$, —NH—C(=NH)—$NH_2$, —SH, —$SCH_3$, —COOH, —C(O)$NH_2$, and phenyl which can be optionally substituted with —OH, imidazole, indole;

$R_{27}$ is H or $C_{1-4}$ alkyl;

$R_{28}$ is H, $C_{1-4}$ alkyl, —S(O)$_2$—$C_{1-4}$alkyl, —C(=O)-$C_{1-4}$ alkyl, —C(=NH)—$NH_2$, —C(=O)—C(H$R_{26}$)—$NR_{27}R_{27}$ t is 0, 1;

u is 0, 1, 2;

n is 1 or 2; and at each occurrence, alkyl, alkenyl, or cycloalkyl is optionally substituted with 1–3 halo, —OH, —$OC_{1-4}$alkyl.

2. The compound of claim 1, wherein X is F.

3. The compound of claim 2, wherein Y is F.

4. The compound of claim 1, wherein $Z^1$ is —NH—C(O)$R_1$.

5. The compound of claim 4, wherein $R_1$ is selected from $C_{1-4}$alkyl optionally substituted with 1–3 halo.

6. The compound of claim 5, wherein $R_1$ is $C_{1-4}$alkyl substituted with 1–2 halo.

7. The compound of claim 1, wherein $Z^1$ is —NH—C(S)$R_1$.

8. The compound of claim 7, wherein $R_1$ is selected from $C_{1-4}$alkyl optionally substituted with 1–3 halo.

9. The compound of claim 8, wherein $R_1$ is $C_{1-4}$alkyl substituted with 1–2 halo.

10. The compound of claim 1, wherein $Y^1$ is —C(=O)— and $X^1$ is —N($R_5$)—.

11. A compound selected from the group consisting of
N-({(5S)-3-[3-fluoro-4-(6-oxopiperidin-3-yl)phenyl]-2-oxo-1,3-oxazolidin-5-yl}methyl)acetamide;
N-({(5S)-3-[3-fluoro-4-(6-oxopiperidin-3-yl)phenyl]-2-oxo-1,3-oxazolidin-5-yl}methyl)propanamide;
2,2-dichloro-N-({(5S)-3-[3-fluoro-4-(6-oxopiperidin-3-yl)phenyl]-2-oxo-1,3-oxazolidin-5-yl}methyl)acetamide;
2,2-difluoro-N-({(5S)-3-[3-fluoro-4-(6-oxopiperidin-3-yl)phenyl]-2-oxo-1,3-oxazolidin-5-yl}methyl)ethanethioamide;

2,2-difluoro-N-({(5S)-3-[3-fluoro-4-(6-oxopiperidin-3-yl)phenyl]-2-oxo-1,3-oxazolidin-5-yl}methyl)acetamide;
N-({(5S)-3-[3,5-difluoro-4-(6-oxopiperidin-3-yl)phenyl]-2-oxo-1,3-oxazolidin-5-yl}methyl)acetamide;
2,2-dichloro-N-({(5S)-3-[3,5-difluoro-4-(6-oxopiperidin-3-yl)phenyl]-2-oxo-1,3-oxazolidin-5-yl}methyl)acetamide;
N-({(5S)-3-[3,5-difluoro-4-(6-oxopiperidin-3-yl)phenyl]-2-oxo-1,3-oxazolidin-5-yl}methyl)-2,2-difluoroethanethioamide;
N-({(5S)-3-[3,5-difluoro-4-(6-oxopiperidin-3-yl)phenyl]-2-oxo-1,3-oxazolidin-5-yl}methyl)-2,2-difluoroacetamide;
N-({(5S)-2-oxo-3-[4-(6-oxopiperidin-3-yl)phenyl]-1,3-oxazolidin-5-yl}methyl)acetamide;
N-({(5S)-2-oxo-3-[4-(6-oxopiperidin-3-yl)phenyl]-1,3-oxazolidin-5-yl}methyl)propanamide;
2,2-dichloro-N-({(5S)-2-oxo-3-[4-(6-oxopiperidin-3-yl)phenyl]-1,3-oxazolidin-5-yl}methyl)acetamide;
2,2-difluoro-N-({(5S)-2-oxo-3-[4-(6-oxopiperidin-3-yl)phenyl]-1,3-oxazolidin-5-yl}methyl)ethanethioamide;
2,2-difluoro-N-({(5S)-2-oxo-3-[4-(6-oxopiperidin-3-yl)phenyl]-1,3-oxazolidin-5-yl}methyl)ethanethioamide;
({(5S)-3-[4-(1-methyl-6-oxopiperidin-3-yl)phenyl]-2-oxo-1,3-oxazolidin-5-yl}methyl)acetamide;
N-({(5S)-3-[3-fluoro-4-(2-oxopiperidin-4-yl)phenyl]-2-oxo-1,3-oxazolidin-5-yl}methyl)acetamide;
N-({(5S)-3-[3-fluoro-4-(2-oxopiperidin-4-yl)phenyl]-2-oxo-1,3-oxazolidin-5-yl}methyl)propanamide;
2,2-difluoro-N-({(5S)-3-[3-fluoro-4-(2-oxopiperidin-4-yl)phenyl]-2-oxo-1,3-oxazolidin-5-yl}methyl)ethanethioamide;
N-({(5S)-3-[3,5-difluoro-4-(2-oxopiperidin-4-yl)phenyl]-2-oxo-1,3-oxazolidin-5-yl}methyl)acetamide;
N-({(5S)-3-[3,5-difluoro-4-(2-oxopiperidin-4-yl)phenyl]-2-oxo-1,3-oxazolidin-5-yl}methyl)propanamide;
N-({(5S)-3-[3,5-difluoro-4-(2-oxopiperidin-4-yl)phenyl]-2-oxo-1,3-oxazolidin-5-yl}methyl)-2,2-difluoroethanethioamide;
N-({(5S)-2-oxo-3-[4-(2-oxopiperidin-4-yl)phenyl]-1,3-oxazolidin-5-yl}methyl)acetamide;
2,2-difluoro-N-({(5S)-2-oxo-3-[4-(2-oxopiperidin-4-yl)phenyl]-1,3-oxazolidin-5-yl}methyl)ethanethioamide;
N-({(5S)-2-oxo-3-[4-(2-oxopiperidin-4-yl)phenyl]-1,3-oxazolidin-5-yl}methyl)propanamide; and
N-({(5S)-3-[4-(1-methyl-2-oxopiperidin-4-yl)phenyl]-2-oxo-1,3-oxazolidin-5-yl}methyl)acetamide.

12. A compound selected from the group consisting of
N-({(5S)-3-[3-fluoro-4-(6-oxopiperidin-3-yl)phenyl]-2-oxo-1,3-oxazolidin-5-yl}methyl)acetamide;
N-({(5S)-3-[3-fluoro-4-(6-oxopiperidin-3-yl)phenyl]-2-oxo-1,3-oxazolidin-5-yl}methyl)propanamide;
N-({(5S)-3-[3,5-difluoro-4-(6-oxopiperidin-3-yl)phenyl]-2-oxo-1,3-oxazolidin-5-yl}methyl)acetamide;
N-({(5S)-2-oxo-3-[4-(6-oxopiperidin-3-yl)phenyl]-1,3-oxazolidin-5-yl}methyl)acetamide;
N-({(5S)-2-oxo-3-[4-(6-oxopiperidin-3-yl)phenyl]-1,3-oxazolidin-5-yl}methyl)propanamide;
({(5S)-3-[4-(1-methyl-6-oxopiperidin-3-yl)phenyl]-2-oxo-1,3-oxazolidin-5-yl}methyl)acetamide;
N-({(5S)-3-[3-fluoro-4-(2-oxopiperidin-4-yl)phenyl]-2-oxo-1,3-oxazolidin-5-yl}methyl)acetamide;
N-({(5S)-3-[3-fluoro-4-(2-oxopiperidin-4-yl)phenyl]-2-oxo-1,3-oxazolidin-5-yl}methyl)propanamide;
N-({(5S)-3-[3,5-difluoro-4-(2-oxopiperidin-4-yl)phenyl]-2-oxo-1,3-oxazolidin-5-yl}methyl)acetamide;
N-({(5S)-3-[3,5-difluoro-4-(2-oxopiperidin-4-yl)phenyl]-2-oxo-1,3-oxazolidin-5-yl}methyl)propanamide;
N-({(5S)-2-oxo-3-[4-(2-oxopiperidin-4-yl)phenyl]-1,3-oxazolidin-5-yl}methyl)acetamide;
N-({(5S)-2-oxo-3-[4-(2-oxopiperidin-4-yl)phenyl]-1,3-oxazolidin-5-yl}methyl)propanamide; and
N-({(5S)-3-[4-(1-methyl-2-oxopiperidin-4-yl)phenyl]-2-oxo-1,3-oxazolidin-5-yl}methyl)acetamide.

13. A compound selected from the group consisting of
2,2-dichloro-N-({(5S)-3-[3-fluoro-4-(6-oxopiperidin-3-yl)phenyl]-2-oxo-1,3-oxazolidin-5-yl}methyl)acetamide;
2,2-difluoro-N-({(5S)-3-[3-fluoro-4-(6-oxopiperidin-3-yl)phenyl]-2-oxo-1,3-oxazolidin-5-yl}methyl)ethanethioamide;
2,2-difluoro-N-({(5S)-3-[3-fluoro-4-(6-oxopiperidin-3-yl)phenyl]-2-oxo-1,3-oxazolidin-5-yl}methyl)acetamide;
2,2-dichloro-N-({(5S)-3-[3,5-difluoro-4-(6-oxopiperidin-3-yl)phenyl]-2-oxo-1,3-oxazolidin-5-yl}methyl)acetamide;
N-({(5S)-3-[3,5-difluoro-4-(6-oxopiperidin-3-yl)phenyl]-2-oxo-1,3-oxazolidin-5-yl}methyl)-2,2-difluoroethanethioamide;
N-({(5S)-3-[3,5-difluoro-4-(6-oxopiperidin-3-yl)phenyl]-2-oxo-1,3-oxazolidin-5-yl}methyl)-2,2-difluoroacetamide;
2,2-dichloro-N-({(5S)-2-oxo-3-[4-(6-oxopiperidin-3-yl)phenyl]-1,3-oxazolidin-5-yl}methyl)acetamide;
2,2-difluoro-N-({(5S)-2-oxo-3-[4-(6-oxopiperidin-3-yl)phenyl]-1,3-oxazolidin-5-yl}methyl)ethanethioamide;
2,2-difluoro-N-({(5S)-2-oxo-3-[4-(6-oxopiperidin-3-yl)phenyl]-1,3-oxazolidin-5-yl}methyl)ethanethioamide;
2,2-difluoro-N-({(5S)-3-[3-fluoro-4-(2-oxopiperidin-4-yl)phenyl]-2-oxo-1,3-oxazolidin-5-yl}methyl)ethanethioamide;
N-({(5S)-3-[3,5-difluoro-4-(2-oxopiperidin-4-yl)phenyl]-2-oxo-1,3-oxazolidin-5-yl}methyl)-2,2-difluoroethanethioamide; and
2,2-difluoro-N-({(5S)-2-oxo-3-[4-(2-oxopiperidin-4-yl)phenyl]-1,3-oxazolidin-5-yl}methyl)ethanethioamide.

14. A method for the treatment of microbial infections in mammals comprising administration of an effective amount of compound of claim 1 to said mammal.

15. The method of claim 14 wherein said compound of claim 1 is administered to the mammal orally, parenterally, transdermally, or topically in a pharmaceutical composition.

16. The method of claim 15 wherein said compound is administered in an amount of from about 0.1 to about 100 mg/kg of body weight/day.

17. The method of claim 15 wherein said compound is administered in an amount of from about 1 to about 50 mg/kg of body weight/day.

18. A pharmaceutical composition comprising a compound of claim 1 and a pharmaceutically acceptable carrier.

* * * * *